(12) United States Patent
Deorazio et al.

(10) Patent No.: US 6,683,101 B2
(45) Date of Patent: Jan. 27, 2004

(54) BICYCLIC CYCLOHEXYLAMINES AND THEIR USE AS NMDA RECEPTOR ANTAGONISTS

(75) Inventors: Russell Joseph Deorazio, Schenectady, NY (US); Sham Shridhar Nikam, Ann Arbor, MI (US); Ian Leslie Scott, Delanson, NY (US); Brian Alan Sherer, Clifton Park, NY (US); Lawrence David Wise, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 10/297,263

(22) PCT Filed: May 14, 2001

(86) PCT No.: PCT/US01/15605
§ 371 (c)(1), (2), (4) Date: Dec. 3, 2002

(87) PCT Pub. No.: WO01/94321
PCT Pub. Date: Dec. 13, 2001

(65) Prior Publication Data
US 2003/0232810 A1 Dec. 18, 2003

Related U.S. Application Data

(60) Provisional application No. 60/209,485, filed on Jun. 6, 2000.

(51) Int. Cl.⁷ .................. A61K 31/4184; A61K 31/423; C07D 235/26; C07D 263/58
(52) U.S. Cl. .................. 514/375; 514/387; 544/49; 544/52; 544/105; 544/235; 544/285; 544/354; 548/165; 548/207; 548/221; 548/257; 548/304.4; 548/306.4; 548/362.5; 548/484; 548/486; 548/491; 548/503

(58) Field of Search .............................. 548/221, 306.4; 514/375, 387

(56) References Cited

U.S. PATENT DOCUMENTS 6,069,176 A * 5/2000 Tsuchiya et al. ............. 514/646
6,184,236 B1 * 2/2001 Alanine et al. ............. 514/329
2003/0004212 A1 * 1/2003 DeOrazio et al. ........... 514/485

FOREIGN PATENT DOCUMENTS

| EP | 0599203 | 6/1994 |
|---|---|---|
| EP | 0982026 | 3/2000 |
| WO | 9948891 | 9/1999 |

OTHER PUBLICATIONS

PCT International Search Report, PCT/US01/15605.

* cited by examiner

*Primary Examiner*—Flona T. Powers
(74) *Attorney, Agent, or Firm*—Charles W. Ashbrook; David R. Kurlandsky

(57) ABSTRACT

Described are heterocycle-substituted cyclohexylamines of formula (I), and their pharmaceutically acceptable salts thereof. The compounds of the formula (I) are antagonists of NMDA receptor channel complexes useful for treating cerebral vascular disorders such as, for example, cerebral ischemia, cardiac arrest, stroke, and Parkinson's disease,

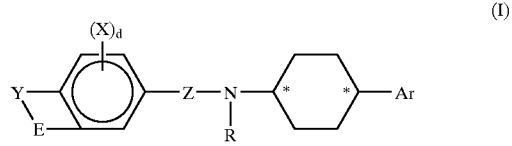

(I)

25 Claims, No Drawings

BICYCLIC CYCLOHEXYLAMINES AND THEIR USE AS NMDA RECEPTOR ANTAGONISTS

This application claims the benefit of PCT/US01/15605 filed May 14, 2001, which claims the benefit of U.S. Provisional Application No. 60/209,485 filed Jun. 6, 2000; the entire contents of each of which are hereby incorporated herein by reference.

FIELD OF INVENTION

The invention pertains to heterocycle-substituted cyclohexylamine derivatives as N-Methyl-D-Aspartate Antagonists (NMDA).

BACKGROUND OF THE INVENTION

Over excitation of NMDA receptor channel complexes on postsynaptic neurons following excessive release of glutamic acid from synaptosomes and glutamic acid from synaptosomes and glial cells result in a massive calcium ion influx into the neuronal cells, which leads to their death. This is believed to occur under ischemic or hypoxic conditions such as stroke, hypoglycemic, cardiac arrest and physical trauma An NMDA receptor antagonist might be therapeutically useful because it may minimize damage of the central nervous system induced by ischemic or hypoxic conditions. The NMDA receptor channel complex consists of at least three binding domains including glutamic acid (or NMDA) recognition site, channel blocking binding site, and strycinine-insensitive glycine binding type. Physiologically, a blockade of at least one of these sites terminates the channel opening of the NMDA receptor to prevent a calcium ion influx (Nagata tm et al., *J. Med Chem.*, 1994;37:3956–3968).

Excessive excitation by neurotransmitters may be responsible for the loss of neurons in cerebral vascular disorders such as cerebral ischemia or cerebral infauxtion resulting in a range of conditions such as thromboembolic or hemorrhagic stroke, cerebral vasospasmn, hypoglycemia, cardiac arrest, status epilepticus, prenatal, asphyxia anoxia, such as from near drowning, pulmonary surgery, and cerebral trauma, as well as lathyrism, Alzeimer's disease, and Huntington's disease. Such conditions likewise suggest the use of agents that may act as antagonists in the receptors identified above may lead to treatment of amyotrophic lateral sclerosis (ALS), schizophrenia, parkinsonism, epilepsy, anxiety, pain, and drug addiction. PCT/EPO 94/01492 having publication number WO 94/26747 published Nov. 24, 1994, Watjen et al.

L-glutamic acid, L-aspartic acid and a number of other closely related amino acids have the ability to activate neurons in the nervous system and therefor the vast majority of excitatory neurons in the mammalian CNS. Interaction with glutamic acid mediated neurotransmission is considered a useful approach in the treatment of neurological and psychiatric diseases. WO 94/26746, published Nov. 24, 1994, Jacobsen, et al.

Excitatory amino acid receptor antagonists that block NMDA receptors are recognized for usefulness in the treatment of a variety of disorders. NMDA receptors are intimately involved in the phenomenon of excitotoxicity, which may be a critical determinant of outcome of several neurological disorders. Disorders known to be responsive to blockade of the NMDA receptor include acute cerebral ischemia (stroke or cerebral trauma, for example), muscular spasm, convulsive disorders, neuropathic pain and anxiety, and may be a significant causal factor in chronic neurodegenerative disorders such as Parkinson's disease (Klockgether T., Turski L. *Ann. Neurol.*, 1993;34:585–593), human immunodeficiency virus (HI) related neuronal injury, amyotrophic laterial sclerosis (ALS), Alzheimer's disease (Francis P. T. Sims N. R, Procter A. W., Bowen D. M. *J Neurochem.*, 1993;60(5):1589–1604), and Huntington's disease (see Lipton S. *TINS*, 1993;16(12):527–532; Lipton S. A., Rosenberg P. A. *New Eng. J. Med*, 1994;330(9): 613–622; and Bigge C. F. *Biochem. Pharmacol.*, 1993;45:1547–1561 and references cited therein). NMDA receptor antagonists may also be used to prevent tolerance to opiate analgesia or to help control withdrawal symptoms from addictive drugs (European Patent Application 488, 959A).

Many of the properties of native NMDA receptors are seen in recombinant homomeric NR1 receptors. These properties are altered by the NR2 subunits. Recombinant NMDA receptors expressed in Xenopus Oocytes have been studied by voltage-clamp recording, and has developmental and regional expression of the mRNAs encoding NMDA receptor subunits. Electrophysiological assays were utilized to characterize the actions of compounds at NMDA receptors expressed in Xenopus Oocytes. The compounds were assayed at four subunit combinations at cloned rat NMDA receptors, corresponding to three putative NMDA receptor subtypes (Moriyoshi et al. *Nature*, 1991; 354:31–37; Monyer et al. *Science*, 1992;256:1217–1221; Kutsuwada et al. *Nature*, 1992; 358:36–41; Sugihara et al. *Biochem. Biophys Res. Comnmun.*, 1992;185:826–832).

Expression cloning of the first NMDA receptor subunit, NMDAR1 (NR1) in Nakanishi's lab in 1991 provided an initial view of the molecular structure of the NMDA receptor (Moriyoshi, supra., 1991). There are several other structurally related subunits (NMDAR2A through NMDAR2D) that join NR1 in heteromeric assemblies to form the functional ion channel complex of the receptor (*Annu. Rev. Neurosci.*, 1994:17;31–108). The molecular heterogeneity of NMDA receptors implies a future potential for agents with subtype selective pharmacology.

SUMMARY OF THE INVENTION

Described are heterocycle-substituted cyclohexylamines of Formula I and their pharmaceutically acceptable salts thereof

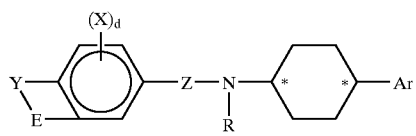

wherein:
Ar is substituted 1 to 3 times or unsubstituted aryl or substituted 1 to 3 times or unsubstituted hereroaryl, which heteroaryl is from 5 to 14 atoms having from 1 to 2 heteroatoms selected from N, O, and S wherein the substituents are selected from the groups F, Cl, Br, I, OH, $NH_2$, SH, CN, $NO_2$, $OCH_3$, $OC(O)CH_3$, $CF_3$, $OCH_2CH_2OH$, $NHC(O)CH_3$, $NHCH_3$, or $N(CH_3)_2$;
—E—Y— is selected from the group consisting of
—CH=CH—N(H)—,
—$(CH_2)_2$—N(H)—,
—CH=N—N(H)—,
—C(O)—$CH_2$—N(H)—, —CH₂—C(O)—N(H)—,
—CH₂—S(O)—N(H)—,
—CH₂—S(O)₂—N(H)—,
—CH=CH—CH(OH)—,
—(CH₂)₂—CH(OH)—,
—C(O)—CH₂—C(O)—,
—C(O)—NH—C(O)—,
—N=CH—N(H)—,
—N(H)—C(O)—N(H)—,
—O—C(O)—NH—,
—S—C(O)—NH—,
—O—N=CH(OH)—,
—S—N=CH(OH)—,
—N=N—N(H)—,
—CH=CH—CH=C(OH)—,
—(CH₂)₃—CH(OH)—,
—(CH₂)₂—S(O)—N(H)—,
—(CH₂)₂—S(O)₂—N(H)—,
—CH=CH—C(O)—N(H)—,
—C(O)—NH—N=C(OH)—,
—CH=N—NH—C(O),
—CH=N(O)—N=C(OH)—,
—N(H)—C(O)—N(H)—C(O)—,
—N=CH—C(O)—NH—,
—O—CH₂—C(O)—NH—,
—S—CH₂—C(O)—NH—, and
—N(H)—C(O)—C(O)—N(H)—;

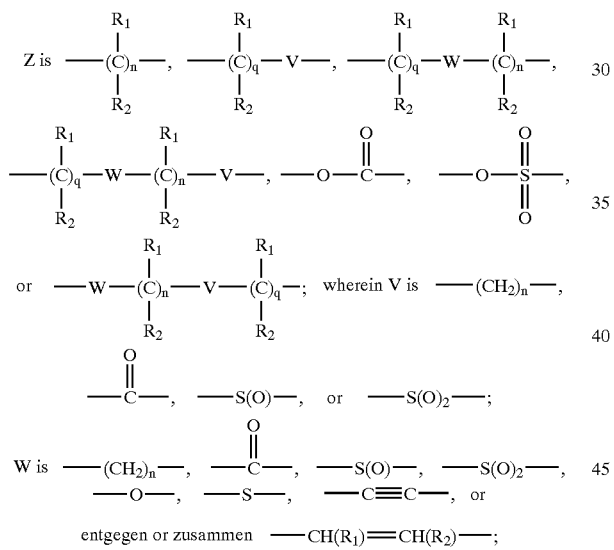

d is an integer from 0 to 2;
n is an integer from 1 to 6;
q is an integer from 0 to 6;
R₁ and R₂ are independently selected from the group consisting of hydrogen, alkyl, OH, hydroxyalkyl, aminoalkyl, aralkyl, or N(R₄)(R₅) wherein R₄ and R₅ are independently selected from hydrogen, alkyl, aralkyl, heteroaryl, heteroaralkyl, aminoalkyl, hydroxyalkyl, and thioalkyl;
R is hydrogen, alkyl, C(O)R₆, C(O)OR₆, C(O)NHR₆, -alkyl-C(O)NH₂, aralkyl, (C₃-C₇ cyclo-alkyl)-alkyl, hydroxyalkyl, aminoalkyl, amino(hydroxy)alkyl, carboxyalkyl, heteroalkyl, alkenylalkyl, or OH wherein R₆ is alkyl or aralkyl;
X is independently selected from hydrogen or an electron withdrawing group; and * denotes cis or trans or a mixture thereof.

The invention also relates to compounds of Formula II

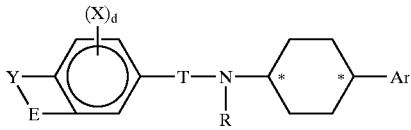

or a pharmaceutically acceptable salt thereof
wherein:
Ar is substituted 1 to 3 times or unsubstituted aryl or substituted 1 to 3 times or unsubstituted heteroaryl, which heteroaryl is from 5 to 14 atoms having from 1 to 2 heteroatoms selected from N, O, and S wherein the substituents are selected from the groups F, Cl, Br, I, OH, NH₂, SH, CN, NO₂, OCH₃, OC(O)CH₃, CF₃, OCH₂CH₂OH, NHC(O)CH₃, NHCH₃, or N(CH₃)₂;
—E—Y— is selected from the group consisting of
—CH=CH—N(H)—,
—(CH₂)₂—N(H)—,
—CH=N—N(H)—,
—C(O)—CH₂—N(H)—,
—CH₂—C(O)—N(H)—,
—CH₂—S(O)—N(H)—,
—CH₂—S(O)₂—N(H)—,
—CH=CH—CH(OH)—,
—(CH₂)₂—CH(OH)—,
—C(O)—CH₂—C(O)—,
—C(O)—NH—C(O)—,
—N=CH—N(H)—,
—N(H)—C(O)—N(H)—,
—O—C(O)—NH—,
—S—C(O)—NH—,
—O—N=CH(OH)—,
—S—N=CH(OH)—,
—N=N—N(H)—,
—CH=CH—CH=C(OH)—,
—(CH₂)₃—CH(OH)—,
—(CH₂)₂—S(O)—N(H)—,
—(CH₂)₂—S(O)₂—N(H)—,
—CH=CH—C(O)—N(H)—,
—C(O)—NH—N=C(OH)—,
—CH=N—NH—C(O),
—CH=N(O)—N=C(OH)—,
—N(H)—C(O)—N(H)—C(O)—,
—N=CH—C(O)—NH—,
—O—CH₂—C(O)NH—,
—S—CH₂—C(O)—NH—, and
—N(H)—C(O)—C(O)—N(H)—;

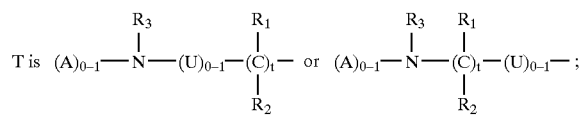

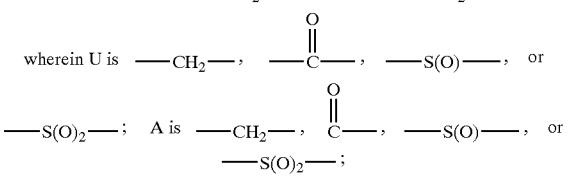

d is an integer from 0 to 2;
t is an integer from 1 to 3;
R₁ and R₂ are independently selected from hydrogen, alkyl, OH, hydroxyalkyl, aminoalkyl, thioalkyl, aryl, aralkyl, heteroaryl, heteroaralkyl, guanidinyl, (aminocarbonyl)alkyl-, carboxyalkyl-, (methylthio)alkyl-, or $N(R_4)(R_5)$ wherein $R_4$ and $R_5$ are independently selected from hydrogen, alkyl, aralkyl, heteroaryl, heteroaralkyl, ureidoalkyl, aminoalkyl, hydroxyalkyl, or thioalkyl;

$R_3$ is hydrogen, alkyl, OH, or aralkyl;

R is hydrogen, alkyl, $C(O)R_6$, $C(O)OR_6$, $C(O)NHR_6$, -alkyl-$C(O)NH_2$, aralkyl, ($C_3$–$C_7$ cyclo-alkyl)-alkyl, hydroxyalkyl, aminoalkyl, amino(hydroxy)alkyl, carboxyalkyl, heteroaralikyl, alkenylalkyl, or OH wherein $R_6$ is alkyl or aralkyl;

X is independently selected from hydrogen or an electron withdrawing group; and * denotes cis or trams or a mixture thereof.

The invention also relates to compounds of Formula III where the substituents E—Y, X, d, R, $R_1$, $R_2$, W, V, and Ar are as defined for Formula I.

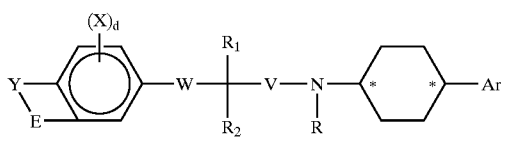

III

The invention is also concerned with a pharmaceutical composition useful for treating disorders responsive to the selective blockade of N-methyl-D-aspartate receptor subtypes in a mammal, including a human, suffering therefrom which comprises a therapeutically effective amount of at least one compound of Formula I or Formula II or Formula III and the pharmaceutically acceptable salts thereof, optionally disorders as stroke, cerebral ischemia, trauma, hypoglycemia, neurodegenerative disorders, anxiety, depression, migraine headache, convulsions, aminoglycoside antibiotics-induced hearing loss, psychosis, glaucoma, CMV retinitis, opioid tolerance or withdrawal, chronic pain, or urinary incontinence.

The invention is also concerned with a method of treating disorders responsive to the selective blockade of the N-methyl-D-aspartate receptor subtypes in a mammal, including a human, suffering therefrom which comprises administering in unit dosage form, at least one compound represented by Formulas I–III or their pharmaceutically acceptable salts thereof.

DETAILED DESCRIPTION OF THE INVENTION

In the compounds of the present invention preferred are compounds of Formula I or pharmaceutically acceptable salts thereof. More preferably are those compounds wherein:

X is independently selected from hydrogen or an electron withdrawing group selected from the group consisting of halogen, nitro, cyano, aminoalkyl, $CF_3$, $C(O)CH_3$, and haloalkyl.

More preferred are compounds of Formula I or pharmaceutically acceptable salts thereof wherein:

Ar is unsubstituted or substituted phenyl;

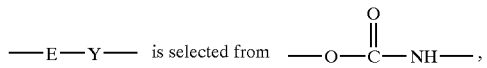

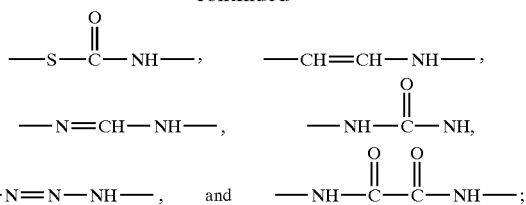

X is independently selected from hydrogen or an electron withdrawing group selected from the group consisting of halogen, nitro, cyano, aminoalkyl, $CF_3$, $C(O)CH_3$, and haloalkyl; and

* denotes trans.

Still more preferred are compounds of Formula I or pharmaceutically acceptable salts thereof wherein:

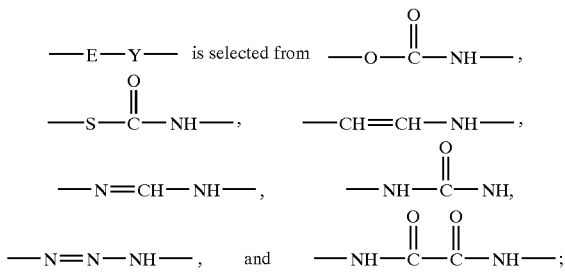

Ar is unsubstituted or substituted phenyl;

Z is as defined above and further a group whereby Ar and the nitrogen atom in Formula I are separated by from 2 to 4 atoms;

X is hydrogen or an electron withdrawing group selected from the group consisting of halogen, nitro, cyano, aminoalkyl, alkyl, $CF_3$, $C(O)CH_3$, and haloalkyl; and

* denotes trans.

Still more preferred are compounds of Formula I or pharmaceutically acceptable salts thereof wherein:

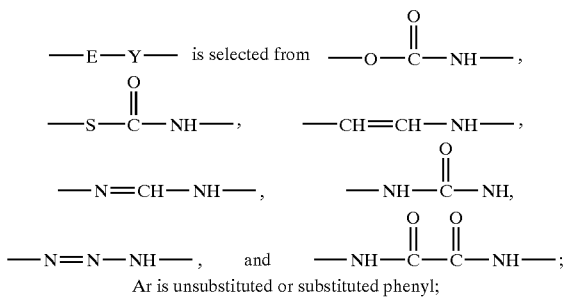

Ar is unsubstituted or substituted phenyl;

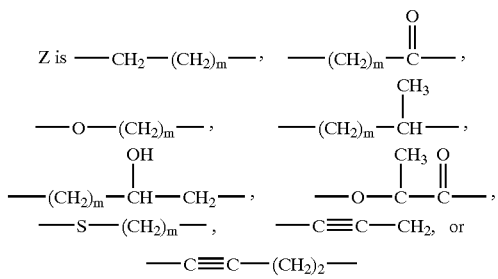

wherein m is an integer from 1 to 3;

R is hydrogen, methyl, $C(O)CH_3$, heteroaralkyl, ($C_3$–$C_7$ cycloalkyl) alkyl, $H_2NC(O)$ alkyl, or alkenylalkyl;

X is hydrogen; and

* denotes trans.

Also preferred is a compound of Formula I wherein * denotes cis.

Most preferred is a compound selected from those listed below:

6-[3-(trans-4-Phenylcyclohexylamino)propyl]-3H-benzoxazol-2-one;

6-{3-[trans-4-(4-Fluorophenyl)cyclohexylamino]propyl}-3H-benzoxazol-2-one;

6-[2-(trans-4-Phenylcyclohexylamino)ethylsulfanyl]-3H-benzoxazol-2-one;

5-{1-Hydroxy-2-[methyl(trans-4-phenylcyclohexyl)amino]ethyl}-1,3-dihydrobenzimidazol-2-one;

6-(3-{[trans-4-(4-Fluorophenyl)cyclohexyl]methylamino}propyl)-3H-benzoxazol-2-one;

6-(3-{[trans-4-(4-Fluorophenyl)cyclohexyl]ethylamino}propyl)-3H-benzoxazol-2-one;

5-[2-(cis-4-Phenylcyclohexylamino)ethoxy]-1,3-dihydrobenzimidazol-2-one;

5-[2-(trans-4-Phenylcyclohexylamino)ethoxy]-1,3-dihydrobenzimidazol-2-one; and

6-{Methyl[2-(trans-4-Phenylcyclohexylamino)ethyl]amino}-3H-benzoxazol-2-one.

Preferred are compounds of Formula II or pharmaceutically acceptable salts thereof wherein:

X is independently selected from hydrogen or an electron withdrawing group selected from the group consisting of halogen, nitro, cyano, aminoalkyl, $CF_3$, $C(O)CH_3$, and haloalkyl.

More preferred are compounds of Formula II or pharmaceutically acceptable salts thereof wherein:

Ar is unsubstituted or substituted phenyl;

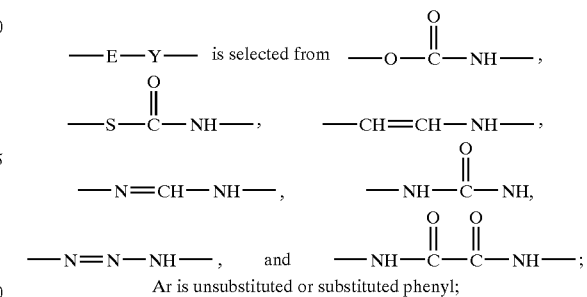

X is independently selected from hydrogen or an electron withdrawing group selected from the group consisting of halogen, nitro, cyano, aminoalkyl, $CF_3$, $C(O)CH_3$, and haloalkyl; and

* denotes trans.

Still more preferred are compounds of Formula II or phamaceutically acceptable salts thereof wherein:

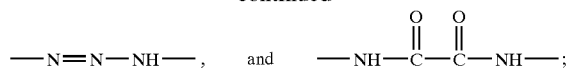

Ar is unsubstituted or substituted phenyl;

Ar and the nitrogen atom bearing R are separated by 3 or 4 atoms;

X is independently selected from hydrogen or an electron withdrawing group selected from the group consisting of halogen, nitro, cyano, $CF_3$, $C(O)CH_3$, and haloalkyl; and

* denotes trans.

Still more preferred are compounds of Formula II or pharmaceutically acceptable salts thereof wherein:

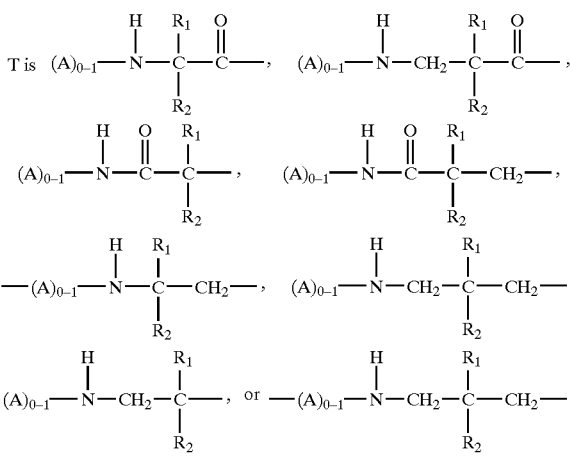

R is hydrogen, $C(O)CH_3$, $H_2NC(O)$ alkyl, alkenylalkyl, or methyl or heteroaralkyl or cycloalkyl (3–7 carbon atoms) alkyl;

X is hydrogen; and

* denotes trans.

Also preferred is a compound of Formula II wherein * denotes cis.

Another preferred compound is that of Formula II named 6-{methyl-[2-(4-phenyl-cyclohexylamino)-ethyl]-amino}-3H-benzoxazol-2-one.

Preferred are compounds of Formula III wherein:

X is independently selected from hydrogen or an electron withdrawing group selected from the group consisting of halogen, nitro, cyano, aminoalkyl, $CF_3$, $C(O)CH_3$, and haloalkyl.

Other preferred compounds of Formula III are wherein:
Ar is unsubstituted or substituted phenyl;

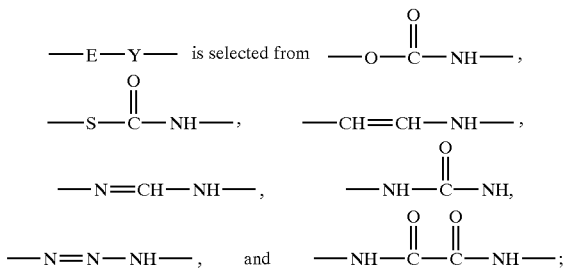

X is independently selected from hydrogen or an electron withdrawing group selected from the group consisting of halogen, nitro, cyano, aminoalkyl, $CF_3$, $C(O)CH_3$, and haloalkyl; and
* denotes cis.

Other preferred compounds of Formula m are wherein:
Ar is unsubstituted or substituted phenyl;

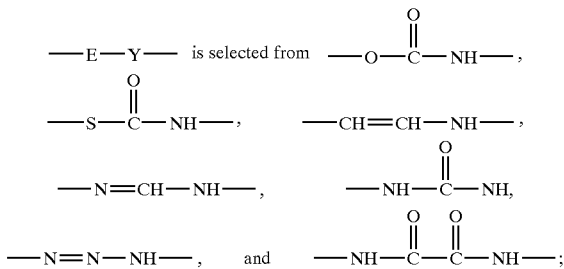

X is independently selected from hydrogen or an electron withdrawing group selected from the group consisting of halogen, nitro, cyano, aminoalkyl, $CF_3$, $C(O)CH_3$, and haloalkyl; and
* denotes trans.

Other preferred compounds of Formula I, II or III are wherein * denotes cis.

The diradical group E—Y must contain a hydrogen bond donor functionality.

The term "alkyl" means a straight or branched hydrocarbon radical having from 1 to 12 carbon atoms unless otherwise specified, also known as a $C_1$–$C_{12}$ alkyl, and includes, for example, methyl, ethyl, 1-propyl, and 2-propyl, 1-butyl, 2-butyl, 2-methyl-1-propyl, 1,1-dimethylethyl, 1-pentyl, 2-pentyl, 3-pentyl, 2,2-dimethylpropyl, 1-hexyl, 2-hexyl, 3-hexyl, 4-methyl-1-pentyl, 1-heptyl, 2-heptyl, 3-heptyl, 4-heptyl, 5-methyl-1-hexyl, 1-octyl, 2-octyl, 3-octyl, 4-octyl, 6-methyl-1-heptyl, 5,5-dimethylhexyl, 1-nonyl, 2-nonyl, 1-decyl, 2-decyl, 1-undecyl, 2-undecyl, 1-dodecyl, and 5-dodecyl. Alkyl groups may be unsubstituted or independently substituted by from 1 to 3 substituents selected from F, Cl, Br, I, OH, $NH_2$, SH, CN, $NO_2$, $OCH_3$, $OC(O)CH_3$, $CF_3$, $OCH_2CH_2OH$, $NHC(O)CH_3$, $NHCH_3$, or $N(CH_3)_2$.

Alkyl groups having two or more carbons may optionally contain 1 or 2 sites of unsaturation, the groups being known as alkenyl groups or radicals. Illustrative examples of an alkenyl group or radical having from 2 to 12 carbon atoms, also known as a $C_2$ to $C_{12}$ alkenyl, include ethenyl, 1-propenyl, 2-propenyl, 1-buten-1-yl, 2-buten-1-yl, 1-penten-1-yl, 2-penten-1-yl, 1-penten-3-yl, 1-penten-5-yl, 1-hexen-1-yl, 1-hexen4-yl, 2-hexen-1-yl, 3-hexen-1-yl, 2-octen-3-yl, 5-nonen-2-yl, 4undecen-1-yl, and 5-dodecen-2-yl.

The term "aryl" means an aromatic carbocyclic ring having from 6 to 10 carbon atoms. Illustrative examples of an aryl group or radical include phenyl, 1-naphthyl, and 2-naphthyl. Aryl groups may be unsubstituted or independently substituted by from 1 to 3 substituents selected from F, Cl, Br, I, OH, $NH_2$, SH, CN, $NO_2$, $OCH_3$, $OC(O)CH_3$, $CF_3$, $OCH_2CH_2OH$, $NHC(O)CH_3$, $NHCH_3$, or $N(CH_3)_2$.

The term "aralkyl" means an aryl-alkyl-group or radical wherein aryl and alkyl have the meanings as defined above. Illustrative examples of an arylalkyl group or radical include benzyl, 4-fluorophenylmethyl, 2-phenylethyl, 3-phenylpropyl, 4-phenylbutyl, 3-methyl-3-phenylpropyl, 1-naphthylmethyl, 1-naphthylethyl, 3-(1-naphthyl)-propyl, 4-(1-naphthyl)-butyl, 4-(2-naphthyl)-butyl, 4-phenylheptyl, and 12-(2-hydroxyphenyl)-dodec-3-yl.

The term "($C_3$–$C_7$ cycloalkyl) alkyl" and "cycloalkyl (3–7 carbon atoms) alkyl" means an "alkyl" group (as described above) substituted thereon by a cycloalkyl group of from 3 to 7 carbon atoms as cyclopentyl, cyclopropyl, cyclohexyl, or cycloheptyl.

The term "heteroatom" means nitrogen, oxygen, or sulfur.

The term "heteroaryl" means an unsaturated monocyclic group or radical of 5 or 6 atoms, an unsaturated fused bicyclic group or radical of from 8 to 10 atoms, or an unsaturated fused tricyclic group or radical of from 11 to 14 atoms, the cyclic groups having 1 or 2 heteroatoms independently selected from O, N, or S. Heteroaryl does not contain a hydrogen bond donor group E—Y. Illustrative examples of monocyclicheteroaryl include 2- or 3-thienyl, 2- or 3-furanyl, 1-pyrrolyl, 1-imidazolyl, 1-pyrazolyl, 2-, 4-, or 5-oxazolyl, 2-, 4-, or 5-thiazolyl, 3-, 4-, or 5-isoxazolyl, 3-, 4-, or 5-isothiazolyl, 2-, 3-, or 4-pyrid 3- or 4-pyridazinyl, 2- or 3-pyrazinyl, and 2-, 4-, or 5-pyrimidinyl. Illustrative examples of bicyclicheteroaryl include 2-, 3-, 4-, 5-, 6-, 7-, or 8-quinolinyl, 1-, 3-, 4-, 5-, 6-, 7-, or 8-isoquinolinyl, 1-indolyl, 2-, 3-, 4-, 5-, 6-, or 7-benzo[b]-thienyl, 2-, 4-, 5-, 6-, or 7-benzofuran, 2-, 4-, 5-, 6-, or 7-benzoxazolyl, 2-, 4-, 5-, 6-, or 7-benzothiazolyl, and 1-benzimidazolyl. Illustrative examples of tricyclic heteroaryl include 1-, 2-, 3-, or 4-dibenzofuranyl, 1-, 2-, 3-, or 4-dibenzothienyl and 1-, 2-, 3-, 4-, 5-, 6-, 7-, 8-, or 9-(1,2,3,4-tetrahydroacridinyl). All with the proviso that when Z in Formula I is attached via a heteroatom, Z is attached to a carbon atom of the heteroaryl group or radical. Heteroaryl groups may be unsubstituted or independently substituted by from 1 to 3 substituents selected from F, Cl, Br, I, OH, $NH_2$, SH, CN, $NO_2$, $OCH_3$, $OC(O)CH_3$, $CF_3$, $OCH_2CH_2OH$, $NHC(O)CH_3$, $NHCH_3$, or $N(CH_3)_2$.

As used above, a fused bicyclic group or radical is a group wherein two ring systems share two and only two atoms.

As used above, a fused tricyclic group or radical is a group wherein three ring systems share four and only four atoms.

The term "heteroarallyl" means a heteroaryl-alkyl-group or radical wherein heteroaryl and alkyl have the meanings as defined above. Illustrative examples of an heteroaralkyl group or radical include 4-pyridyl-methyl, (4-fluoroquinolin-2-yl)methyl, 2-(isoxazol-3-yl)ethyl, and 12-(5-chlorothiophen-2-yl)-dodec-3-yl.

The term "halogen" means bromine, chlorine, fluorine, or iodine.

The term "alkenylalkyl" means a ($C_2$–$C_{12}$ alkenyl)-($C_1$–$C_{12}$ alkyl) group or radical wherein $C_1$–$C_{12}$ alkyl and $C_2$–$C_{12}$ alkenyl are as defined above.

The term "aminoalkyl" means an $H_2N$-alkyl-group or radical wherein alkyl has the meaning as defined above, which is a substituted alkyl group or radical containing from 1 to 3 substituents wherein at least one substituent is —$NH_2$.

The term "hydroxyalkyl" means an HO-alkyl-group or radical wherein alkyl has the meaning as defined above, which is a substituted alkyl group or radical containing from 1 to 3 substituents wherein at least one substituent is —OH.

The term "amino(hydroxy)alikyl" means an $H_2N(HO)$-alkyl-group or radical wherein alkyl has the meaning as defined above, which is a substituted alkyl group or radical containing from 2 or 3 substituents wherein at least one substituent is OH and one substituent is —$NH_2$.

The term "(aminocarbonyl)alkyl" means an $H_2NC(O)$-alkyl-group or radical wherein alkyl has the meaning as defined above, which is a substituted alkyl group or radical containing from 1 to 3 substituents wherein at least one substituent is —(O)C—$NH_2$.

The term "thioalkyl" means an HS-alkyl-group or radical wherein alkyl has the meaning as defined above, which is a substituted alkyl group or radical containing from 1 to 3 substituents wherein at least one substituent is —SH.

The term "(methylthio)-alkyl-" means a $CH_3S$-alkyl-group or radical wherein alkyl has the meaning as defined above, which is a substituted alkyl group or radical containing from 1 to 3 substituents wherein at least one substituent is —$SCH_3$.

The term "carboxyalkyl" means an $HO_2C$-alkyl-group or radical wherein alkyl has the meaning as defined above, which is a substituted alkyl group or radical containing from 1 to 3 substituents wherein at least one substituent is —$CO_2H$.

The term "haloalkyl" means a halogen-alkyl-group or radical wherein halogen and alkyl have the meanings as defined above, which is a substituted alkyl group or radical containing from 1 to 3 substituents wherein at least one substituent is selected from F, Cl, Br, or I.

The term "ureidoalkyl" means an $H_2N$—(C=O)—NH-alkyl-group or radical wherein alkyl has the meanings as defined above, which is a substituted alkyl group or radical containing from 1 to 3 substituents wherein at least one substituent is $H_2N$—(C=O)—NH—.

The term "electron withdrawing group" means a group or radical selected from halogen, nitro, cyano, alkyl, $CF_3$, $C(O)CH_3$, $P(O)(O—R_9)_2$, $SO_2$—$R_9$, $SO_2NHR_9$, $C(O)NR_9R_9'$, wherein $R_9$ is independently selected from $C_1$–$C_6$ alkyl or unsubstituted or substituted phenyl, —(C=NH)—$NH_2$, —(C=NH)—O-alkyl, methoxymethyl, or haloalkyl, wherein the substituents may be F, Cl, Br, I, OH, $NH_2$, SH, CN, $NO_2$, $OCH_3$, $OC(O)CH_3$, $CF_3$, $OCH_2CH_2OH$, $NHC(O)CH_3$, $NHCH_3$, or $N(CH_3)_2$.

The phrase "heterocycle, which heterocycle is a carboxylic acid or an amide isostere" means a 5- or 6-membered monocyclic ring containing from 1 to 4 heteroatoms selected from N, O, and S and providing a hydrogen bond donor moiety selected from NH, OH, and SH. Illustrative examples include the following structures:

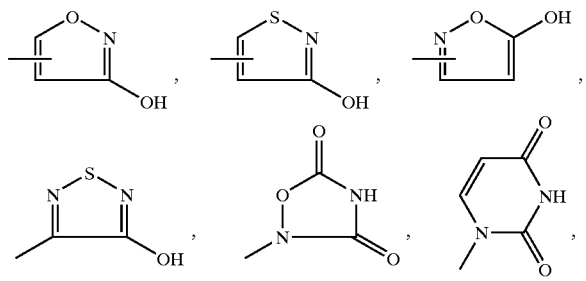

-continued

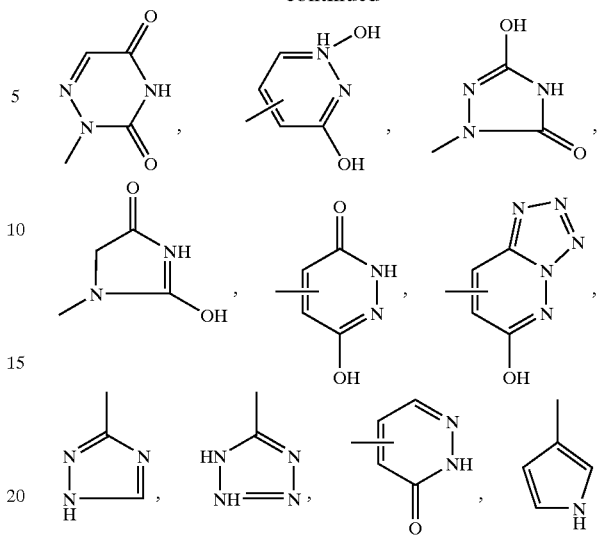

See also Greenwood J. R., Vaccarella G., Cooper H. R., Allan R. D., Johnston G. A. P. *Internet Journal of Chemistry*, 1998;1(38) (Chart 4). Additional examples are well-known to the skilled artisan. (See, for example, (i) Lipinski C. A. *Annual Reports in Medicinal Chemistry*, 1986;21 (Chapter 21, Chapter 27); (ii) Thomber C. W. *Chen. Soc. Rev.*, 1979;8:563; (iii) Burger A. *Progress in Drug Research.*, 1991;37:288–371.)

The term "entgegen" means the stereoisomerism about a carbon-carbon double bond wherein the highest ranking substituent on each carbon are on opposite sides, which substituent ranking is based on the sequence rules of the Cahn-Ingold-Prelog system (March J., *Advanced Organic Chemistry*, 4th ed, John Wiley & Sons, New York, 1992:109, 127, and references cited therein).

The term "zusammen" means the stereoisomerism about a carbon-carbon double bond wherein the highest ranking substituent on each carbon are on the same side, which substituent ranking is based on the sequence rules of the Cahn-Ingold-Prelog system (March J. *Advanced Organic Chemistry*, 4th ed., John Wiley & Sons, New York, 1992:109, 127, and references cited therein).

The term "cis" means the stereoisomerism about a carbon-carbon double bond, a monocyclic ring, a fused bicyclic ring, or a bridged bicyclic ring wherein the highest ranking substituent on each of the two carbons of relevance are on the same side, which substituent ranking is based on the sequence rules of the Cahn-Ingold-Prelog system (March J. *Advanced Organic Chemistry*, 4th ed., John Wiley & Sons, New York, 1992;109, 127–133, and references cited therein).

The term "trans" means the stereoisomerism about a carbon-carbon double bond, a monocyclic ring, a fused bicyclic ring, or a bridged bicyclic ring wherein the highest ranking substituent on each of the two carbons of relevance are on opposite sides, which substituent ranking is based on the sequence rules of the Cahn-Ingold-Prelog system (March J. *Advanced Organic Chemistry*, 4th ed., John Wiley & Sons, New York, 1992:109, 127–133, and references cited therein).

The terms "cis" or "trans" refers to the relative stereochemistry of the groups attached to the cyclohexyl rings of Formulas I or II at the carbon atoms denoted by "*".

The term "$(X)_d$" means the group X is present 1 or 2 times on the phenylene to which it is attached, which group is independently selected from hydrogen or an electron withdrawing group wherein the electron withdrawing group is as defined above unless otherwise stated. The groups X can be the same or different.

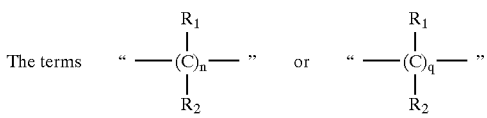

wherein n is an integer of from 1 to 6 and q is an integer of from 0 to 6 mean a chain of from 1 to 6 carbons or from 0 to 6 carbons, respectively, wherein each carbon is independently substituted, which substituents are the groups $R_1$ and $R_2$, wherein $R_1$ and $R_2$ are independently ($R_1$ and $R_2$ in each occurrence can be the same or different) selected from the groups consisting of hydrogen, alkyl, OH, hydroxyalkyl, aminolkyl, aralkyl, or $N(R_4)(R_5)$ wherein $R_4$ and $R_5$ are independently selected from hydrogen, alkyl, aralkyl, heteroaryl, heteroaralkyl, aminoalkyl, hydroxyalkyl and thioalkyl, unless otherwise stated. The groups $R_1$ can be the same or different and the groups $R_2$ can be the same or different.

For purposes of the syntheses of the compounds of the present invention, reactive functional groups present in starting materials, reaction intermediates, or reaction products may be protected during chemical reactions using protecting groups which render the reactive functional groups substantially inert to the reaction conditions (see for example, Green T. W., Wuts P. G. *Protective Groups in Organic Synthesis*, 2nd ed., John Wiley & Sons, New York, 1991). Thus, for example, protecting groups such as the following may be utilized to protect suitable amino, hydroxyl, and other groups of related reactivity: carboxylic acyl groups, such as formyl, acetyl, trifluoroacetyl; alkoxycarbonyl groups, such as ethoxycarbonyl, t-butoxycarbonyl (BOC), β,β,β-trichloroethoxycarbonyl (TCEC), β-iodoethoxycarbonyl; aryloxycarbonyl groups, such as benzyloxycarbonyl, p-methoxybenzyloxycarbonyl, phenoxycarbonyl; trialkyl silyl groups, such as trimethylsilyl and t-butyldimethylsilyl (TBDMS); and groups such as trityl, tetrahydropyranyl, vinyloxycarbonyl, o-nitrophenylsulfenyl, diphenylphosphinyl, p-toluenesulfonyl, and benzyl may all be utilized. The protecting group may be removed, after completion of the synthetic reaction of interest, by procedures known to those skilled in the art. For example, a BOC group may be removed by acidolysis, a trityl group by hydrogenolysis, TBDMS by treatment with fluoride ions, and TCEC by treatment with zinc.

It is to be appreciated that the compounds of Formulas I–III may have chiral centers in which case, all stereoisomers thereof both separately and as racemic and/or diastereoisomeric mixtures are included.

Some of the compounds of Formulas I–III are capable of further forming pharmaceutically acceptable acid-addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihyrogenphosphate, metaphosphate, pyrophosphate, chloride, bromide, iodide, acetate, trifluoroacetate, propionate, caprylate, isobutyrate, oxalate, malonate, succinates suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, malate, tartrate, methanesulfonate, and the like. Also contemplated are salts of amino acids such as arginate and the like and gluconate, galacturonate (see, for example, Berge S. M. et al. "Pharmaceutical Salts," *Journal of Pharmaceutical Science*, 1977;66:1–19).

The acid addition salt of said basic compounds are prepared by contacting the free base form with a sufficient amount of the desired acid to produce the salt in the conventional manner.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N-dibenzylethylenediainine, chloroprocaine, choline, diethanolamine, dicyclohexylamine, ethylenediamine, N-methylglucamine, and procaine (see, for example, Berge, supra., 1977).

The base addition salts of said acidic compounds are prepared by contacting the free acid form with a sufficient amount of the desired base to produce the salt in the conventional manner.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formulas I–III or a corresponding pharmaceutically acceptable salt of a compound of Formulas I–III.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding properties in suitable proportions and compacted in the shape and size desired.

The powders and tablets preferably contain from 5 or 10 to about 70 percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted, and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, and stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is divided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use as antagonists or as agents for the treatment of diseases, the compounds utilized in the pharmaceutical method of this invention are administered at the initial dosage of about 0.01 mg to about 100 mg/kg daily. A daily dose range of about 0.01 mg to about 10 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages, which are less than the optimum dose of the compound. Thereafter, the dosage is increased by small increments until the optimum effect under the circum stances is reached. For convenience, the total daily dosage may be divided and administered in portions during the day, if desired.

| Tablet Formulation | |
|---|---|
| Ingredient | Amount (mg) |
| Example 1 | 25 |
| Lactose | 50 |
| Cornstarch (for mix) | 10 |
| Cornstarch (paste) | 10 |
| Magnesium stearate (1%) | 5 |
| Total | 100 |

Example 1, lactose and cornstarch (for mix) are blended to uniformity. The cornstarch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets can be administered to a human from one to four times a day for treatment of disease caused by over excitation of NMDA receptor channel complexes.

The compounds of the present invention can be prepared according to the various synthetic schemes that follow. Protecting groups may be used when appropriate throughout many of the schemes. Although specifically noted in certain schemes, the appropriate use and choice of protecting groups is well-known by one skilled in the art, and is not limited to the specific examples below. It is also understood that such groups not only serve to protect chemically reactive sites, but also to enhance solubility or otherwise change physical properties. A good general reference for protecting group preparation and deprotection is "Protective Groups in Organic Synthesis" by Theodora Green, supra, 1991. A number of general reactions such as oxidations and reductions are not shown in detail but can be done by methods understood by one skilled in the art. General transformations are well reviewed in "Comprehensive Organic Transformation" by Richard Larock, and the series "Compendium of Organic Synthetic Methods" (1989) published by Wiley-Interscience. In general, the starting materials were obtained from commercial sources unless otherwise indicated.

Preparation of Compounds

These compounds can be prepared following the procedures described in the examples below.

General Methods

HCl salts were prepared by treatment of a MeOH solution of the amine with excess HCl in $Et_2O$. The salts were isolated either by filtration if they precipitated directly from the etherial solution, or by first removal of the solvent under reduced pressure, and then crystallization ($Et_2O$/MeOH).

Purity was determined by reversed phase HPLC by the following methods:

Method A: column: YMC J'Sphere C18, ODS-M80, 150×4.6 mm, 4$\mu$; solvent A: 0.1% $H_3PO_4$ in $H_2O$; solvent B: 0.1% $H_3PO_4$ in $CH_3CN$; gradient: 10–100% B over 15 minutes; flow: 1 mL min$^{-1}$; detection: 210 nm.

Method B: column: YMC J'Sphere C18, ODS-M80, 150×4.6 mm, 4$\mu$; solvent A: 0.1% $H_3PO_4$ in $H_2O$; solvent B: 0.1% $H_3PO_4$ in MeOH; gradient: 10–100% B over 15 minutes; flow: 1 mL min$^{-1}$; detection: 210 nm.

EXAMPLE 1

Preparation of 6-[3-(trans-4-Phenylcyclohexylamino)propyl]-3H-benzoxazol-2-one

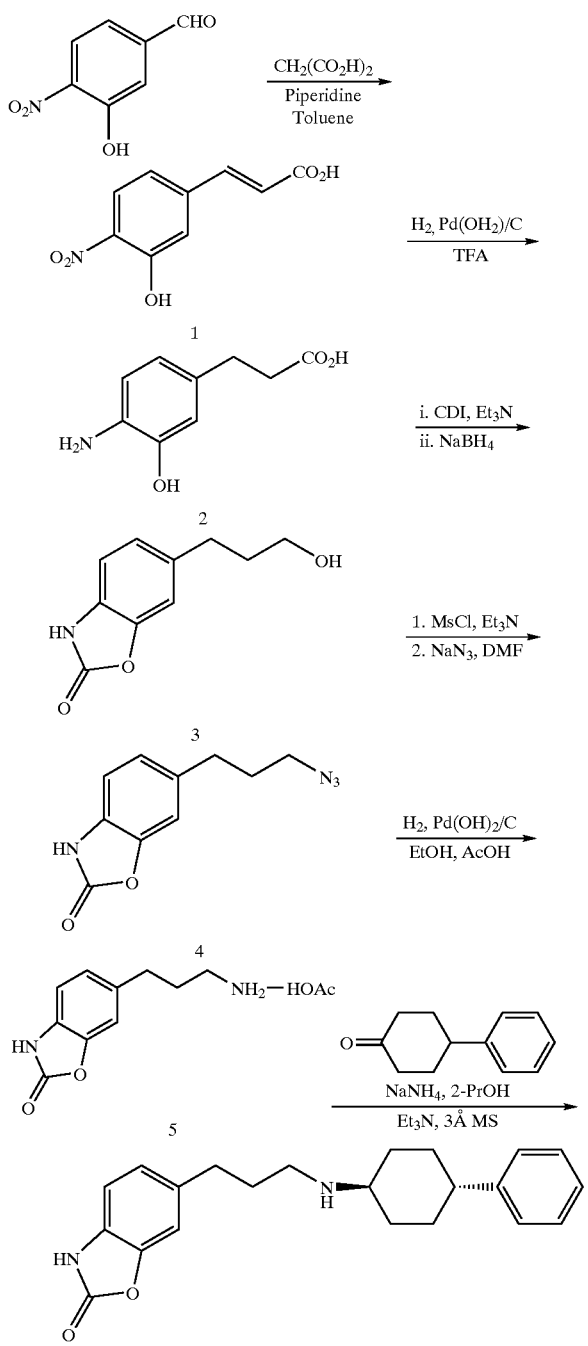

Compound 1:
Beilstein Registry Number 3136644, 3301556; CAS Registry Number 90729-86-5 Chakravarti, Ganapati, Aravamudhachari. *J. Chem. Soc.*, 1938:171.

Compound 2:
AN 1984:438944; DN 101:38944; Mathias L. J., Grubb T. L., Tullos G. L. *Polym. Prepr.*, 1983;24:335–336.

Step 1: A mixture of 4-hydroxy-3-nitrobenzaldehyde (9.7 g, 58 mmol), malonic acid (7.25 g, 70 mmol), and piperidine (0.29 mL, 3.0 mmol) in toluene (70 mL) were heated under Dean-Stark conditions overnight. After cooling, the product was extracted into saturated NaHCO$_3$. The solution was filtered and then acidified with 1N HCl. Compound 1 was obtained as a yellow precipitate, which was collected and used without further purification: $^1$H NMR (300 MHz, DMSO-d$_6$): δ 7.80 (d, J=8 Hz, 1H), 7.55 (d, J=15 Hz, 1H), 7.35 (s, 1H), 7.32 (d, J=8 Hz, 1H), 6.60 (d, J=15 Hz, 1H).

Step 2: To a suspension of 1in a mixture of MeOH (60 mL) and H$_2$O (20 mL) was added TFA (5.4 mL, 70 mmol) and 20% Pd(OH)$_2$/C (0.20 g). The mixture was shaken under a H$_2$ atmosphere at 50 psi for 2 hours. Then, the solution was filtered and concentrated under reduced pressure. The product was dissolved in EtOAc, and the solution was dried (MgSO$_4$). Concentration under reduced pressure gave 2 (19.3 g, 100%) as a TFA salt, which was used without further purification: $^1$H NMR (500 MHz, DMSO-d$_6$): δ 7.05 (d, J=8 Hz, 1H), 6.80 (d, J=1 Hz, 1H), 6.69 (dd, J=8, 1 Hz, 1H), 2.74 (t, J=7.5 Hz, 2H), 2.48 (t, J=7.5 Hz, 2H).

Step 3: To an ice-cold solution of compound 2 (19.3 g) in THF (100 mL) was added triethylamine (24.2 mL, 174 mmol) and then carbonyl diimidazole (2×10.3 g, 128 mmol). After 30 minutes, NaBH$_4$ (4.40 g, 116 mmol) was added, followed by H$_2$O (100 mL) dropwise. The solution was acidified with 1N HCl, saturated with NaCl, and extracted with EtOAc. The organic solution was dried (MgSO$_4$) and concentrated under reduced pressure. Purification by flash chromatography (silica, 99:1 CHCl$_3$:MeOH to 9:1 CHCl$_3$:MeOH) gave 3 (9.34 g, 83%): $^1$H NMR (300 MHz, CD$_3$OD): δ 7.04 (s, 1H), 6.96 (m, 2H), 3.61 (t, J=6 Hz, 2H), 2.72 (t, J=7 Hz, 2H), 1.95 (tt, J=7, 6 Hz, 2H).

Step 4: To an ice-cold solution of 3 (9.3 g, 48 mmol) and triethylairine (10 mL, 73 mmol) in THF (100 mL) was added methane sulfonyl chloride (5.2 mL, 65 mmol). The reaction was quenched with H$_2$O and the resultant mixture partitioned between EtOAc and 1N HCl and then filtered through Celite. The organic layer was washed with H$_2$O, saturated NaHCO$_3$, saturated NaCl, dried (MgSO$_4$), and concentrated under reduced pressure. This gave a mixture of products, which were not separated at this stage.

Step 5: A mixture of the crude mesylate (14.7 g), sodium azide (7.00 g, 108 mmol), acetone (200 mL), and H$_2$O (100 mL) were heated under reflux overnight. The mixture was concentrated under reduced pressure, to remove the acetone, and then partitioned between EtOAc and H$_2$O. The organic layer was washed with H$_2$O, saturated NaCl, dried (MgSO$_4$), and concentrated under reduced pressure. Purification by flash chromatography (silica, 3:1 to 2:1 hexanes:EtOAc) gave 4 (3.59 g, 28%): $^1$H NMR (500 MHz, CDCl$_3$): δ 7.03 (s, 1H), 6.98 (s, 2H), 3.31 (t, J=6 Hz, 2H), 2.70 (t, J=7 Hz, 2H), 1.92 (tt, J=7, 6 Hz, 2H).

Step 6: A mixture of 4 (3.59 g, 16.4 mmol), 20% Pd(OH)$_2$/C (0.20 g), AcOH (1.7 mL, 30 mmol), and EtOH (50 mL) were shaken under a H$_2$ atmosphere at 50 psi overnight. The solution was filtered through Celite and then concentrated under reduced pressure. Recrystallization from MeOH/THF gave 5 (2.6 g, 63%), as a pale yellow solid: mp 161–167° C.; $^1$H NMR (500 MHz, DMSO-d$_6$): δ 7.95 (br, 3H), 7.07 (d, J=1 Hz, 1H), 6.95 (d, J=6 Hz, 1H), 6.89 (dd, J=6, 1 Hz, 1H), 2.63 and 2.68 (both d, J=7 Hz, 2H), 1.77 (m, 2H), 1.77 (s, 3H); IR (KBr): 1778, 1716 cm$^{-1}$; CI-MS (methane) (m/z): 208 [M+H]$^+$.

Step 7: To a stirred solution of 4-phenylcyclohexanone (0.52 g, 2.98 mmol) in 2-propanol (40 mL) was added 3Å molecular sieves and compound 5 (0.75 g, 2.98 mmol). To the reaction mixture was added a catalytic amount of triethylamine and, after 4 hours, sodium borohydride (0.16 g, 4.17 mmol). The reaction mixture was stirred overnight. The reaction mixture was quenched with MeOH and concentrated under reduced pressure. Purification by flash chromatography gave 6-[3-(trans-4-phenylcyclohexylamino)propyl]-3H-benzoxazol-2-one (0.40 g, 31%): mp 218–223° C.; IR (KBr): 2930, 1761, 1653, 1583 cm$^{-1}$; 1H NMR (500 MHz, DMSO-d$_6$): δ 7.28–7.11 (m, 7H), 6.95 (s, 1H), 2.63 (t, J=6 Hz, 2H), 2.56 (t, J 6 Hz, 2H), 2.51 (obs m, 2H), 1.95 (d, J=10 Hz, 2H), 1.77 (d, J=10 Hz, 2H), 1.69 (quint, J=7 Hz, 2H), 1.45 (dddd, J=10, 10, 10, 2 Hz, 2H), 1.13 (dddd, J=10, 10, 10, 2 Hz, 2H); API-MS (m/z): 351 [M+H]$^+$; HRMS-API (m/z): [M+H]$^+$ Calcd for $C_{22}H_{26}N_2O_2$, 351.2072; found, 351.2077; HPLC: method A, 7.89 minutes (99.9%); method B, 14.54 minutes (98.7%); Anal. Calcd for $C_{22}H_{26}N_2O_2 \cdot 0.66H_2O$: C, 72.90; H, 7.60; N, 7.73. Found: C, 72.23; H, 7.36; N, 7.37.

EXAMPLE 2

Preparation of 6-{3-[trans-4-(4-Fluorophenyl)cyclohexylamino]propyl}-3H-benzoxazol-2-one

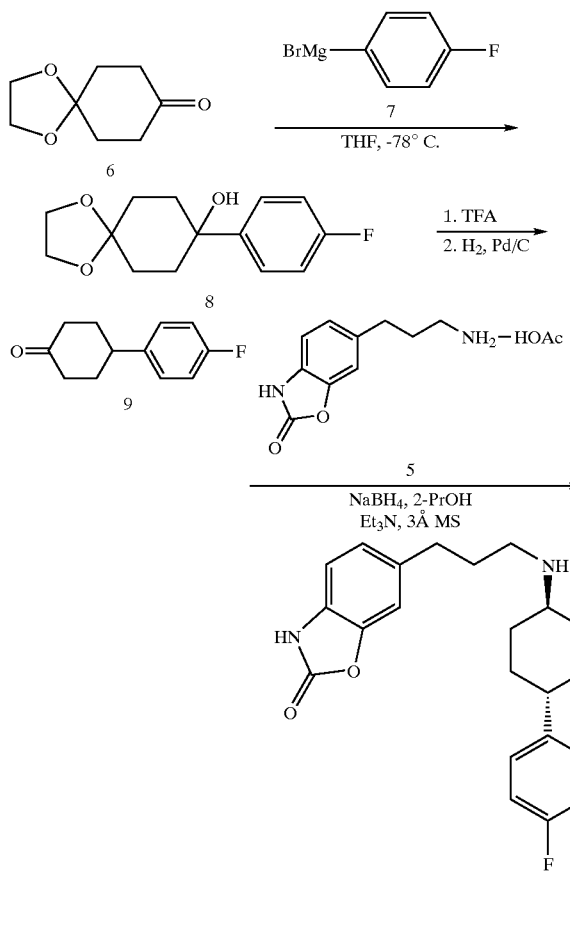

Step 1: Ketal 6 (10.1 g, 64.7 mmol) was dissolved in anhydrous THF (100 mL), and the solution was cooled to −78° C. 4-Fluorophenylmagnesium bromide 7 (78 mL of a 1.0 M solution in THF, 78 mmol) was added slowly over 10 minutes. After 20 minutes, saturated NH$_4$Cl (10 mL) was added and the mixture allowed to warm to room temperature. The mixture was partitioned between CHCl$_3$ and saturated NH$_4$Cl. The organic layer was dried (Na$_2$SO$_4$), filtered through Celite, and concentrated under reduced pressure. Purification by flash chromatography (silica gel, 1:9 to 3:7 EtOAc:hexanes, loaded in a minimum of CH$_2$Cl$_2$) gave 8 (10.9 g, 67%); $^1$H NMR (300 MHz, CDCl$_3$): δ 7.5 (dd, J=8, 8 Hz, 2H), 7.05 (dd, J=8, 8 Hz, 2H), 4.00–3.91 (m, 5H), 2.25–2.08 (m, 4H), 1.85 (d, J=8 Hz, 2H), 1.65 (d, J=8 Hz, 2H).

Step 2: Compound 8 (8.23 g, 32.6 mmol) was stirred in TFA (25 mL) for 15 minutes. The reaction mixture was poured into H$_2$O (100 mL) and then extracted with CHCl$_3$ (2×75 mL). The organic solution was washed with saturated bicarbonate, dried (Na$_2$SO$_4$), filtered, and concentrated under reduced pressure to afford the crude alkene (6.44 g): $^1$H NMR (300 MHz, CDCl$_3$): δ 7.35 (dd, J=8, 8 Hz, 2H), 7.04 (dd, J=8, 8 Hz, 2H), 6.05 (m, 1H), 3.05 (m, 2H), 2.87 (m, 2H), 2.65 (dd, J=7, 7 Hz, 2H).

Step 3: A solution of the crude alkene (6.44 g), 10% Pd/C (0.20 g) in EtOAc (100 mL) was shaken under a H$_2$ atmosphere at 50 psi for 1 hour. The solution was filtered through Celite and concentrated under reduced pressure. Purification by flash chromatography (silica, 1:9 EtOAc:hexanes) gave 9 (5.49 g, 88%) as a pale yellow solid: mp 35–39° C.; IR (KBr): 2935, 1713, 1510 cm$^{-1}$; $^1$H NMR (500 MHz, CDCl$_3$): δ 7.22–7.15 (m, 2H), 7.04–6.96 (m, 2H), 3.02 (dt, J=7, 3 Hz, 1H), 2.55–2.44 (m, 4H), 2.23–2.21 (m, 2H), 1.95–1.86 (m, 2H); CI-MS (methane) (m/z): 193 [M+H]$^+$; HPLC: method A, 11.59 minutes (96.7%).

Step 4: To a solution of ketone 9 (0.23 g, 1.16 mmol) and triethylamine (0.17 mL, 1.16 mmol) in 2-propanol (25 mL) and was added 3 Å molecular sieves and amine 5 (0.39 g, 2.02 mmol). The reaction mixture was stirred overnight. Sodium borohydride (0.062 g, 1.63 mmol) was added and the reaction mixture stirred for 30 minutes before quenching with MeOH. Concentration under reduced pressure, followed by conversion to the HCl salt, gave 6-{3-[trans-4-(4-fluoro-phenyl)cyclohexylamino]propyl}-3H-benzoxazol-2-one as a white solid: (0.125 g, 24%): mp 295–303° C.; IR (KBr): 3262, 2934, 2803, 1781, 1744, 1510 cm$^{-1}$; $^1$H NMR (500 MHz, CD$_3$OD): δ 7.24–7.21 (m, 2H), 7.15 (s, 1H), 7.11–6.95 (m, 4H), 3.19–3.14 (m, 1H), 3.05 (dd, J=8, 6 Hz, 2H), 2.78 (dd, J=8, 8 Hz, 2H), 2.60–2.54 (m, 1H), 2.22 (d, J=10 Hz, 2H), 2.05–1.93 (m, 4H), 1.63–1.50 (m, 4H); MS-CI (methane) (m/z): 369 [M+H]$^+$; HPLC: method A, 7.99 minutes (97.1%); method B, 14.52 minutes (95.0%); Anal. Calcd for $C_{22}H_{25}FN_2O_2 \cdot 0.5NaCl \cdot HCl$: C, 60.87; H, 6.04; N, 6.45. Found: C, 60.80; H, 6.06; N 6.34.

EXAMPLE 3

Preparation of 6-{Methyl[2-(trans-4-phenylcyclohexylamino)ethyl]amino}-3H-benzoxazol-2-one

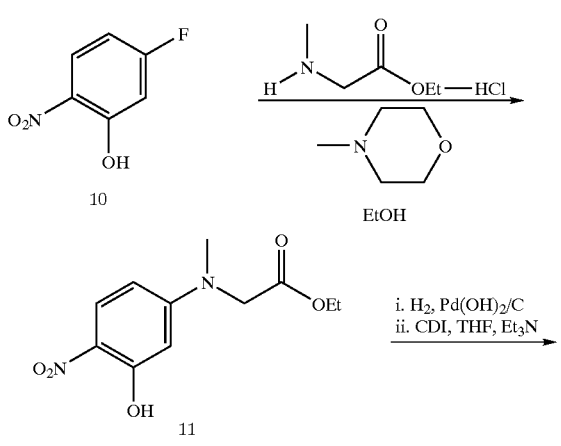

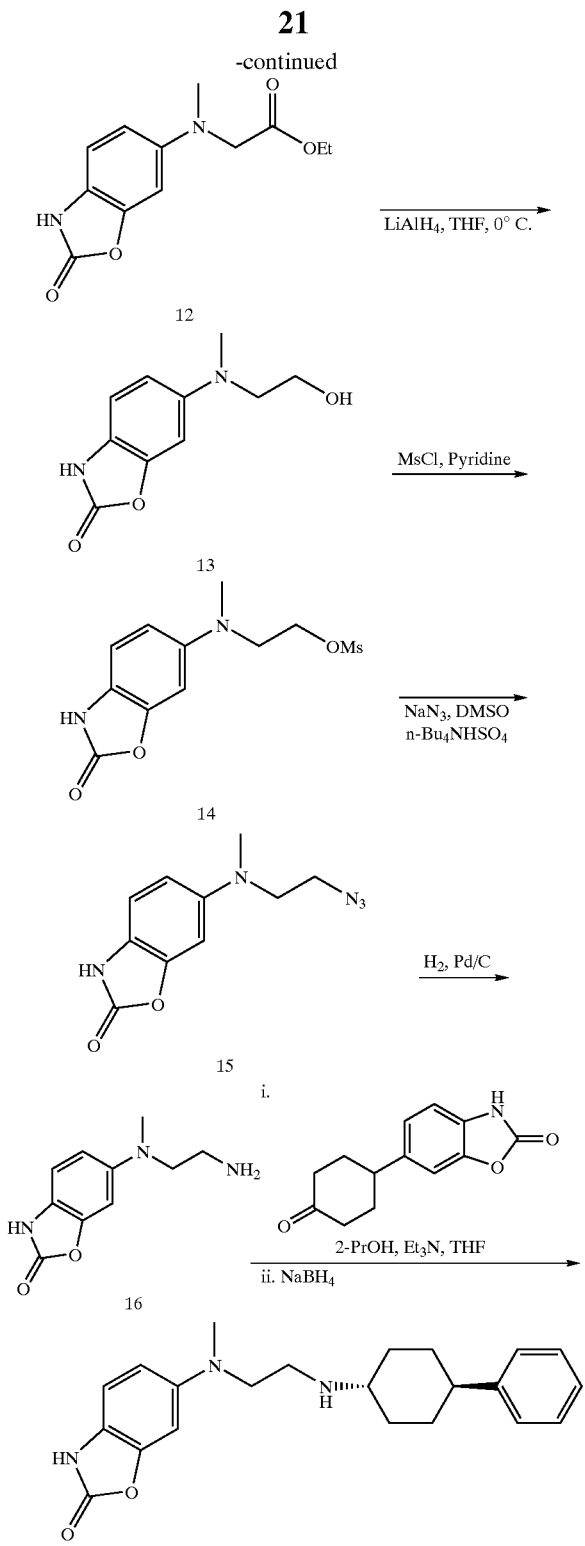

Step 1: To a solution of sarcosine ethyl ester hydrochloride (7.5 g, 49 mmol) in EtOH (150 mL) was added N-methylmorpholine (10.6 mL, 96 mmol) and 5 fluoro-2-nitrophenol 10 (6.4 g, 41 mmol). The mixture was heated under reflux for 4 days. The reaction mixture was cooled and partitioned between EtOAc and 1H HCl. The organic solution was washed with saturated NaCl and dried (MgSO$_4$). Concentration under reduced pressure gave 11 (8.3 g, 81%): $^1$H NMR (500 MHz, CDCl$_3$): δ 7.95 (d, J=9 Hz, 1H), 6.25 (dd, J=9, 2 Hz, 1H), 6.20 (d, J=2 Hz, 1H), 4.24 (q, J=7 Hz, 2H), 4.14 (s, 2H), 3.20 (s, 3H), 1.26 (t, J=7 Hz, 3H).

Step 2: To a solution of 11 (6.0 g, 23 mmol) in EtOH (350 mL) was added TFA (4.5 mL) and 20% Pd(OH)$_2$/C (0.2 g). The reaction mixture was shaken under an atmosphere of H$_2$ at 50 psi for 2 hours. The reaction mixture was then purged with nitrogen, transferred to a round bottom flask, and concentrated under reduced pressure. The vacuum was released to nitrogen, and the residue was dried by concentration from toluene (2×). The residue was dissolved in THF (275 mL) and cooled in an ice/H$_2$O bath. To the cooled, stirred solution was added Et$_3$N (8.2 mL, 59 mmol) and carbonyl diimidazole (4.2 g, 2.6 mmol). The reaction mixture was allowed to warm to room temperature and, after 2.75 hours, was diluted with EtOAc and filtered through Celite. The filtrate was washed with 2N HCl, saturated NaCl, dried (Na$_2$SO$_4$), filtered, and concentrated under reduced pressure. Purification by flash chromatography (silica, 95:5 CH$_2$Cl$_2$:MeOH) gave 12 (3.7 g, 64%), as a dark blue residue: 1H NMR (500 MHz, CD$_3$OD): δ 6.92 (d, J=9 Hz, 1H), 6.73 (d, J=2 Hz, 1H), 6.55–6.57 (m, 1H), 4.18–4.13 (m, 4H), 3.04 (s, 3H), 1.23 (t, J=7 Hz, 3H).

Step 3: A stirred solution of 12 (4.5 g, 18 mmol) in THF (150 mL), under an N$_2$ atmosphere, was cooled in an ice/H$_2$O bath. To this was added LiAlH$_4$ (18 mL of a 1.0 M solution in Et$_2$O, 18 mmol), portionwise, and additional THF (50 mL). After 1 hour, the reaction mixture was quenched by the slow addition of MeOH and warmed to room temperature. The mixture was concentrated under reduced pressure. Purification by flash chromatography (silica, 95:5 and 90:10 CH$_2$Cl$_2$:MeOH) gave compound 13 (2.3 g, 63%): CI-MS (methane) (m/z): 209 [M+H]$^+$.

Step 4: To an ice-cold stirred solution of 13 (2.2 g, 11 mmol) in pyridine (40 mL) was added Et$_3$N (1.3 g, 13 mmol), followed by methanesulfonyl chloride (1.5 g, 13 mmol). After 1.75 hours, the reaction mixture was warmed to room temperature, diluted with EtOAc, washed with 1N HCl, H$_2$O, saturated NaHCO$_3$, saturated NaCl, and dried (Na$_2$SO$_4$). After drying, concentration under reduced pressure gave mesylate 14 (2.8 g, 89%), which was used without further purification: $^1$H NMR (300 MHz, DMSO-d$_6$): δ 6.92 (d, J=9 Hz, 1H), 6.79 (d, J=2 Hz, 1H), 6.51–6.57 (m, 1H), 4.34–4.28 (m, 2H), 3.68–3.60 (m, 2H), 3.13 (s, 3H), 2.90 (s, 3H).

Step 5: A mixture of the mesylate 14 (2.8 g, 10 mmol), NaN$_3$ (1.2 g, 20 mmol), and tetra-n-butylammonium hydrogen sulfate (0.35 g, 1.1 mmol) in DMSO (35 mL) was heated at 40–45° C. for 20 hours. After cooling, the reaction mixture was partitioned between EtOAc and H$_2$O. The organic layer was washed with H$_2$O, then saturated NaCl, and dried (Na$_2$SO$_4$). Concentration under reduced pressure gave azide 15 (1.9 g, 87%), which was used without further purification: $^1$H NMR (300 MHz, CD$_3$OD): δ 6.92 (d, J=9 Hz, 1H), 6.74 (d, J=2 Hz, 1H), 6.55–6.64 (m, 1H), 3.54–3.39 (m, 4H), 2.95 (s, 3H).

Step 6: To a solution of 15 (1.9 g, 8.1 mmol) in EtOH (40 mL) was added AcOH (1 mL) and 20% Pd(OH)$_2$/C (0.10 g). The reaction mixture was shaken under an atmosphere of H$_2$ at 50 psi overnight. The reaction mixture was then purged with N$_2$, filtered through Celite, and concentrated under reduced pressure. Purification by trituration (MeOH/Et$_2$O) gave amine 16 (1.4 g, 66%): CI-MS (methane) (m/z): 208 [M+H]$^+$.

Step 7: To a stirred solution of 16 (0.70 g, 2.6 mmol) in a mixture of 2-propanol (30 mL) and THF (30 mL) was added Et$_3$N (0.29 g, 2.9 mmol), 4-phenylcyclohexanone (0.46 g, 2.6 mmol) and 3 Å molecular sieves. After 2 hours, sodium borohydride (0.14 g, 3.7 mmol) was added, and the reaction mixture was stirred overnight. Additional sodium borohydride was added (0.15 g, 3.8 mmol) and, after 2.25 hours, the reaction mixture was quenched with MeOH, filtered through Celite, and the filtrate was concentrated under reduced pressure. Purification by recrystallization (MeOH/Et$_2$O), and formation of the bis-HCl salt, gave trans-isomer 6-{methyl[2-(trans-4-phenylcyclohexylamino) ethyl]amino}-3H-benzoxazol-2-one (0.16 g, 17%): mp 229–234° C.; IR (KBr): 2938, 1774 cm$^{-1}$; $^1$H NMR (500 MHz, DMSO-d$_6$): δ 9.09 (br s, 2H), 7.31–7.15 (m, 5H), 6.97–6.93 (m, 2H), 6.70–6.67 (m, 1H), 3.67–3.62 (m, 2H), 3.10–3.08 (m, 3H), 2.91 (s, 3H), 2.51–2.50 (obs m, 1H), 2.21–2.17 (m, 2H), 1.90–1.86 (m, 2H), 1.62–1.46 (m, 4H); CI-MS (methane) (m/z): 366 [M+H]$^+$; HPLC: method B, 12.40 minutes (98.7%); Anal. Calcd for C$_{22}$H$_{27}$N$_3$O$_2$.2HCl: C, 60.27; H, 6.67; N, 9.58. Found: C, 60.52; H, 6.70; N, 9.55.

EXAMPLE 4

Preparation of 6-[2-(trans-4-Phenylcyclohexylamino)ethylsulfanyl]-3H-benzoxazol-2-one 45° C. overnight. After cooling, the reaction mixture was partitioned between EtOAc and H$_2$O. The organic layer was washed with H$_2$O, saturated NaCl, dried (Na$_2$SO$_4$), and filtered. Concentration under reduced pressure gave azide 18 (1.0 g, 100%), which was used without further purification: $^1$H NMR (300 MHz, CD$_3$OD): δ 7.44 (d, J=2 Hz, 1H), 7.23 (d, J=2 Hz, 1H), 7.20 (d, J=2 Hz, 1H), 3.45 (t, J=7 Hz, 2H), 3.14 (t, J=7 Hz, 2H).

Step 2: To an ice-cold, stirred solution of 18 (1.0 g, 4.2 mmol) in THF (30 mL), under an N$_2$ atmosphere, was added LiAlH$_4$ (0.16 g, 4.2 mmol) portionwise. The mixture was stirred at room temperature for 3 hours. After re-cooling, the reaction was quenched by the slow addition of H$_2$O, and the solvent was removed under reduced pressure. The residue was partitioned between EtOAc and 1N HCl. The organic solution was separated and brought to pH=14 with solid NaOH. The mixture was saturated with NaCl and extracted with EtOAc (3×). The combined organics were dried (Na$_2$SO$_4$) and concentrated under reduced pressure. The residue was dissolved in MeOH, and an excess of 1.0 M HCl in Et$_2$O was added. The solution was filtered and the filtrate concentrated under reduced pressure. Purification by flash chromatography (silica, 89:10:1 CH$_2$Cl$_2$:MeOH:NH$_4$OH) gave amine 19 (0.26 g, 30%): 1H NMR (300 MHz, CD$_3$OD): δ 7.28 (s, 1H), 7.11 (d, J=8 Hz, 1H), 6.95 (d, J=8 Hz, 1H), 2.91 (t, J=8 Hz, 2H), 2.69 (t, J=7 Hz, 2H).

Step 3: To a stirred solution of 19 (0.25 g, 1.2 mmol) in a mixture of 2-propanol (20 mL) and THF (20 mL) was added 4-phenylcyclohexanone (0.46 g, 2.6 mmol) and 3 Å molecular sieves. After 3 hours, sodium borohydride (0.067 g, 1.8 mmol) was added, and the reaction mixture was stirred overnight. The reaction mixture was quenched with MeOH, filtered through Celite, and the filtrate was concentrated under reduced pressure. The product was purified by flash chromatography (silica, 95:5 CH$_2$Cl$_2$:MeOH) and converted to an HCl salt. Recrystallization from MeOH/Et$_2$O gave the

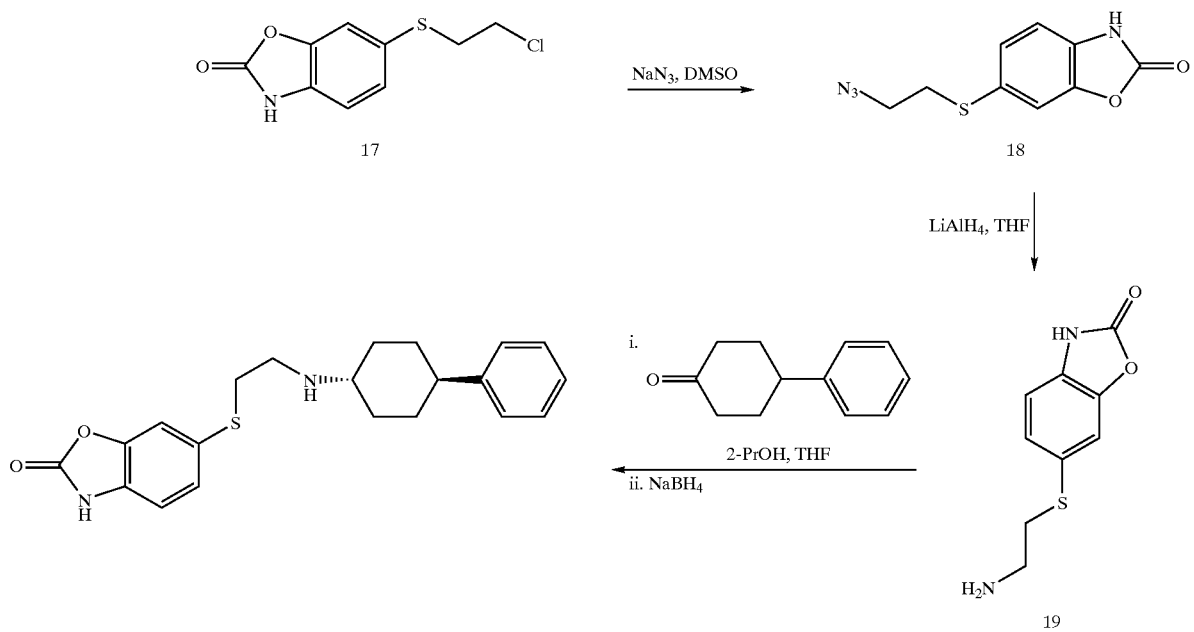

Step 1: A mixture of chloride 17 (1.0 g, 4.3 mmol), NaN$_3$ (1.8 g, 7.8 mmol), and tetra-n-butylammnonium hydrogen sulfate (0.15 g, 4.3 mmol) in DMSO (20 mL) was heated at trans-isomer 6-[2-(trans-4-phenylcyclohexylamino) ethylsulfanyl]-3H-benzoxazol-2-one (0.024 g, 5%): $^1$H NMR (500 MHz, DMSO-d$_6$): δ 9.09 (br s, 2H), 7.45–7.05

(m, 8H), 3.10 (t, J=7 Hz, 2H), 2.93 (t, J=7 Hz, 2H), 2.85–2.75 (m, 1H), 2.55–2.44 (obs m, 2.02 (br d, J=11 Hz, 2H), 1.82 (br d, J=11 Hz, 2H), 1.45 (dddd, J=11, 11, 11, 3 Hz, 2H), 1.29 (dddd, J=II, 11, II, 3 Hz, 2H); CI-MS (methane) (in/z): 369 [M+H]$^+$; HPLC: method A, 6.33 minutes (89.6%); Anal. Calcd for $C_{21}H_{24}N_2O_2S$·HCl: C, 62.29; H, 6.22; N, 6.92. Found: C, 63.34; H, 6.26; N 7.24.

EXAMPLE 5

Preparation of 5-{1-Hydroxy-2-[methyl(trans-4-phenylcyclohexyl)amino]ethyl}-1,3-dihydrobenzimidazol-2-one

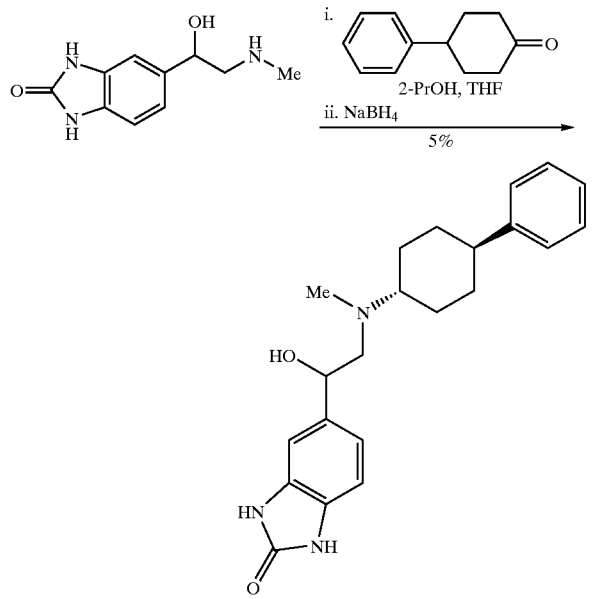

Compound 20: Vaughan J. R., Blodinger J. *J. Am. Chem. Soc.*, 1955;77:5757.

To a stirred solution of 20 (1.1 g, 3.4 mmol) in a mixture of 2-propanol (60 mL) and THF (40 mL) was added Et$_3$N (0.50 mL, 3.4 mmol), 4-phenylcyclohexanone (0.60 g, 3.4 mmol) and 3 Å molecular sieves. After 3 hours, sodium borohydride (0.19 g, 5.1 mmol) was added, and the reaction mixture was stirred overnight. The reaction mixture was quenched with MeOH, filtered through Celite, and the filtrate was concentrated under reduced pressure. The product was purified by flash chromatography (silica, 89:10:1 CH$_2$Cl$_2$:MeOHNH$_4$OH) and recrystallization to give 5-{l-hydroxy-2-[methyl(trans-4-phenylcyclohexyl)amino] ethyl}-1,3-dihydrobenzimidazol-2-one (48 mg, 4%): mp 238–239° C.; IR (KBr): 2925, 1709 cm$^{-1}$; $^1$H NMR (500 MHz, DMSO-d$_6$): δ 10.45 (d, J=12 Hz, 2H), 7.28–7.14 (m, 5H), 6.95–6.82 (m, 3H), 4.67 (s, 1H), 4.57–4.54 (m, 1H), 2.56–2.38 (m, 4H), 2.50 (s, 3H), 1.85–1.76 (m, 4H), 1.49–1.27 (m, 4H); CI-MS (methane) (m/z): 366 [M+H]$^+$; HPLC: method A, 6.15 minutes (95.7%); method B, 9.94 minutes (>99%); Anal. Calcd for $C_{22}H_{27}N_3O_2$: C, 72.30; H, 7.45; N, 11.50. Found: C, 72.07; H, 7.17; N 11.25.

EXAMPLE 6

Preparation of 6-(3-{[trans-4-(4-Fluorophenyl) cyclohexyl]methylamino}propyl)-3H-benzoxazol-2-one

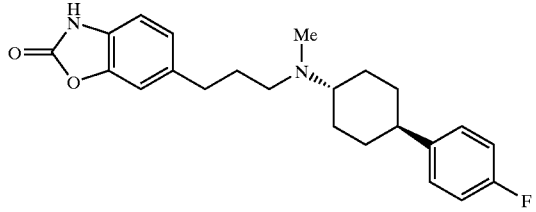

To a stirred solution of 6-{3-[trans-4-(4-fluorophenyl) cyclohexylamino]-propyl}-3H-benzoxazol-2-one (240 mg, 0.652 mmol) in methanol (10 mL) containing water (0.5 mL) was added p-formaldehyde (98 mg, 3.26 mmol). The reaction mixture was stirred for 3 hours, then sodium triacetoxyborohydride (193 mg, 0.913 mmol) was added. The mixture was stirred overnight. Solid NaOH was added to the reaction mixture until a clear solution formed. The reaction mixture was concentrated under reduced pressure. Purification by flash chromatography (silica, 95:5:1 CH$_2$Cl$_2$:MeOH:NH$_4$OH) followed by conversion to an HCl salt gave 6-(3-{[trans-4-(4-Fluorophenyl)cyclohexyl] methylamino}-propyl)-3H-benzoxazol-2-one (145 mg, 53%), as a white solid: mp 235–241° C.; IR (KBr): 3048, 1771 cm$^{-1}$; $^1$H NMR (500 MHz, DMSO-d$_6$): δ 9.66 (br s, 1H), 7.31–7.12 (m, 6H), 7.06 (s, 1H), 3.19–3.14 (m, 1H), 3.05 (dd, J=8, 6 Hz, 2H), 2.78 (dd, J=8, 8 Hz, 2H), 2.74 (s, 3H), 2.60–2.54 (m, 1H), 2.22 (d, J=10 Hz 2H), 2.05–1.93 (m, 4H), 1.63–1.50 (m, 4H); CI-MS (methane) (m/z): 383 [M+H]$^+$; HPLC: method A, 6.28 minutes (97.2%); method B, 10.61 minutes (98.8%); Anal. Calcd for $C_{23}H_{27}FN_2O_2$·HCl·0.5NH$_4$Cl: C, 61.98; H, 6.78; N, 7.86. Found: C, 61.63; H, 6.56; N 7.77.

EXAMPLE 7

Preparation of 6-(3-{[trans-4-(4-Fluorophenyl) cyclohexyl]ethylamino}propyl)-3H-benzoxazol-2-one

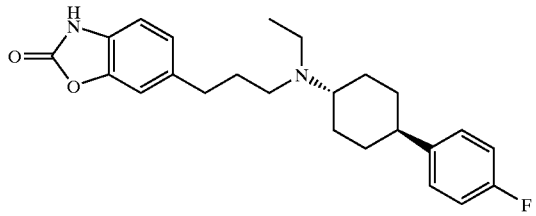

To a stirred solution of 6-{3-[trans-4-(4-fluorophenyl) cyclohexylamino]-propyl}-3H-benzoxazol-2-one (240 mg, 0.652 mmol) in THF (20 mL) was added acetaldehyde (28 mg, 0.652 mmol). The reaction mixture was stirred for 15 minutes, then sodium triacetoxyborohydride (193 mg, 0.913 mmol) was added. The reaction mixture was concentrated under reduced pressure after 45 minutes. The residue that results was dissolved in MeOH (5 mL) and stirred with solid NaOH until the pH was >8. The solution was concentrated under reduced pressure. Purification by flash chromatography (silica, 95:5:1 CH$_2$Cl$_2$:MeOH:NH$_4$OH) and conversion to the HCl salt gave 6-(3-{[trans-4-(4-fluorophenyl) cyclohexyl]ethylamino}propyl)-3H-benzoxazol-2-one (80 mg, 28%), as a white solid: mp 99–109° C.; IR (KBr): 2938, 1772 cm$^{-1}$; $^1$H NMR (500 MHz, DMSO-d$_6$): δ 9.42 (br s, 1H), 7.28–7.15 (m, 6H), 7.07 (s, 1H), 3.24 (m, 2H), 3.17–3.12 (m, 1H), 3.08 (dd, J=8, 6 Hz, 2H), 2.73 (dd, J=8, 8 Hz, 2H), 2.63–2.52 (m, 1H), 2.11 (d, J=10 Hz, 2H), 2.02–1.93 (m, 4H), 1.54-1.46 (m, 4H), 1.28 (m, 3H); CI-MS (methane) (m/z): 397 [M+H]$^+$; HPLC: method A, 6.46 minutes (95.4%); method B, 10.72 minutes (96.1%); Anal. Calcd for C$_{24}$H$_{29}$FN$_2$O$_2$.HCl.0.5H$_2$O: C, 65.22; H, 7.07; N, 6.34. Found: C, 65.24; H, 6.77; N 5.95.

EXAMPLES 8a and 8b

Preparation of 5-[2-(cis-4-Phenylcyclohexylamino) ethoxy]-1,3-dihydrobenzimidazol-2-one 5-[2-(trans-4-Phenylcyclohexylamino)ethoxy]-1,3-dihydrobenzimidazol-2-one

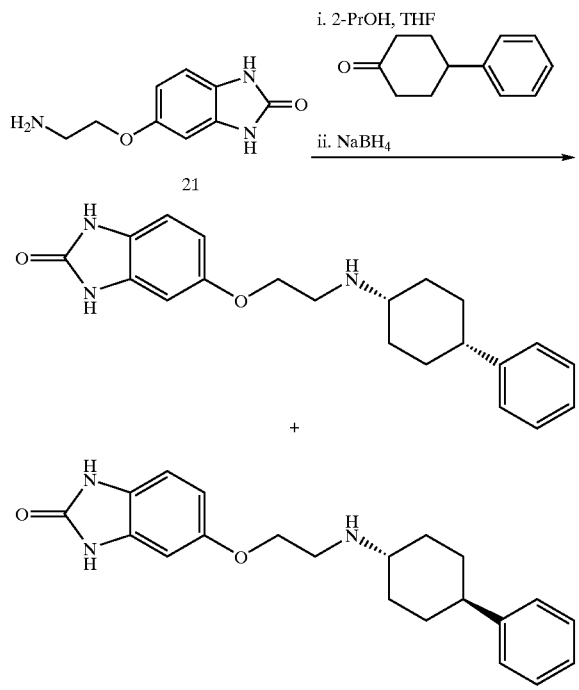

To a stirred suspension of 21 (0.61 g, 3.2 mmol) and 4-phenylcyclohexanone (0.55 g, 3.2 mmol) in 1,2-dichloroethane (20 mL) was added sodium triacetoxyborohydride (0.94 g, 4.4 mmol) and acetic acid (0.18 mL, 3.2 mmol). The reaction mixture was stirred for 20 hours, brought to pH=8 with 2N NaOH, and concentrated under reduced pressure. The isomers were separated and purified by repeated flash chromatography (silica, combinations of CH$_2$Cl$_2$, MeOH, and NH$_4$OH). 5-[2-(cis-4-Phenylcyclohexylamino)ethoxy]-1,3-dihydrobenzimidazol-2-one was isolated as the HCl salt (0.18 g, 12%): mp 232–237° C.; IR (KBr): 2937, 2361, 1696 cm$^{-1}$; $^1$H NMR (300 MHz, CD$_3$OD): δ 7.35–7.27 (m, 4H), 7.20–7.17 (m, 1H), 6.96 (d, J=8 Hz, 1H), 6.76–6.71 (m, 2H), 4.27 (t, J=5 Hz, 2H), 3.52–3.48 (m, 3H), 2.91–2.83 (m, 1H), 2.11–1.96 (m, 6H), 1.96–1.88 (m, 2H); API-MS (m/z): 352 [M+M]$^+$; HRMS-API (m/z): [M+H]$^+$ calcd for C$_{21}$H$_{25}$N$_3$O$_2$, 352.2025; found, 352.2021; HPLC: method A, 5.51 minutes (93.2%); method B, 10.40 minutes (98.6%); Anal. Calcd for C$_{21}$H$_{25}$N$_3$O$_2$.HCl.0.5H$_2$O: C, 63.55; H, 6.86; N, 10.59. Found: C, 63.87; H, 6.82; N, 10.58.

5-[2-(trans-4-Phenylcyclohexylamino)ethoxy]-1,3-dihydrobenzimidazol-2-one was isolated as the HCl salt (0.13 g, 9%): mp 315–320° C.; IR (KBr): 2940, 2363, 1696 cm$^{-1}$; $^1$H NMR (300 MHz, CD$_3$OD): δ 7.32–7.15 (m, 5H), 6.97 (d, J=9 Hz, 1H), 6.79–6.72 (m, 2H), 4.27 (t, J=5 Hz, 2H), 3.52–3.48 (t, J=5 Hz, 2H), 3.31–3.25 (m, 1H), 2.66–2.56 (m, 1H), 2.35–2.27 (m, 2H), 2.10–1.99 (m, 2H), 1.76–1.58 (m, 4H); API-MS (m/z): 352 [M+H]$^+$; HRMS-API (m/z): [M+H]$^+$ calcd for C$_{21}$H$_{25}$N$_3$O$_2$, 352.2025; found, 352.2025; HPLC: method A, 5.54 minutes (93.3%); method B, 10.57 minutes (95.2%); Anal. Calcd for C$_{21}$H$_{25}$N$_3$O$_2$.HCl.0.5H$_2$O: C, 63.55; H, 6.86; N, 10.59. Found: C, 63.70; H, 6.75; N, 10.59.

Electrophysiological Assays at NMDA Receptor Subunits

Preparation of RNA. cDNA clones encoding the NR1A, NR2A, NR2B, and NR2C rat NMDA receptor subtypes were used (see, Moriyoshi et al. *Nature* (Lond), 1991;354:31–37; Kutsuwada et al. *Nature* (Lond), 1992;358:36–41; Monyer et al. Science (Washington, D.C.), 1992;256:1217–1221; Ikeda et al. *FEBS Lett.*, 1992;313:34–38; Ishii et al. *J. Biol. Chem.*, 1993;268:2836–2843 for details of these clones or their mouse homologs). The clones were transformed into appropriate host bacteria, and plasmid preparations were made with conventional DNA purification techniques. A sample of each clone was linearized by restriction enzyme digestion of cRNA and was synthesized with T3 RNA polymerase. The cRNA was diluted to 400 ng/μL and stored in 1 μL aliquots at −80° C. until injection.

The Xenopus oocyte expression system. Mature female Xenopus laevis were anaesthetized (20–40 minutes) using 0.15% 3-aminobenzoic acid ethyl ester (MS-222), and 2–4 ovarian lobes were surgically removed. Oocytes at developmental stages IV–VI (Dumont J. N. *J. Morphol.*, 1972;136:153–180) were dissected from the ovary still surrounded by enveloping ovarian tissues. Follicle-enclosed oocytes were micro-injected with 1:1 mixtures of NR1A:NR2A, 2B, or 2C; injecting 1 to 10 ng of RNA encoding each receptor subunit. NR1A encoding RNA was injected alone at ~20 ng. Oocytes were stored in Barth's medium containing (in mM): NaCl, 88; KCl, 1; CaCl$_2$, 0.41; Ca (NO$_3$)$_2$, 0.33; MgSO$_4$, 0.82; NaHCO$_3$, 2.4; HEPES 5, pH 7.4, with 0.11 mg/ml gentamicin sulphate. While oocytes were still surrounded by enveloping ovarian tissues, the Barth's medium was supplemented with 0.1% bovine serum. Oocytes were defolliculated 1 to 2 days following injections by treatment with collagenase (0.5 mg/mL Sigma Type I for 0.5–1 hour)—(Miledi and Woodward. *J. Phsyiol* (Lond), 1989;416:601–621) and subsequently stored in serum-free medium.

Electrical recordings were made using a conventional two-electrode voltage clamp (Dagan TEV-200) over periods ranging between 3 to 21 days following injection. (Woodward et al. *Mol. Pharmacol.*, 1992;41:89–103). Oocytes were placed in a 0.1 mL recording chamber continuously perfused (5–15 mL min$^{-1}$) with frog Ringer's solution containing (in mM): NaCl, 115; KCl, 2; BaCl$_2$, 1.8; HEPES, 5; pH 7.4. Drugs were applied by bath perfusion. Using oocytes expressing different subunit combinations of NMDA receptor, NMDA currents were activated by co-application of glutamate (100 μM and glycine (1–100 μM). Inhibitory potency of the novel antagonists was assessed on responses elicited by fixed concentrations of glutamate and glycine, by measuring reductions in current induced by progressively increasing concentrations of antagonist.

Concentration-inhibition curves were fit with equation 1.

$$I/I_{control} = 1/(1+([antagonist]/10-pIC_{50})n)$$ Eq. 1

In which $I_{control}$ is the current evoked by agonists alone, $pIC_{50} = -\log IC_{50}$, $IC_{50}$ is the concentration of antagonist that produced half maximal inhibition, and n is the slope factor (De Lean et al. *Am. J. Physiol.*, 1978;235:E97–102). For incomplete curves, analysis by fitting was unreliable, and $IC_{50}$ values were calculated by simple regression over linear portions of the curves (Origin: Microcal Software).

[$^3$H]Ifenprodil Binding Assay Protocol:

MATERIALS and METHODS

All buffers and reagents used in assay incubations or to dissolve drugs were prepared using water purified through a Milli-Q reverse osmosis system (Millipore Corp, Bedford, Mass.) and treated with UV emissions. Prior to use in the assays, buffers were further filtered through a sterile Corning filtration unit (Corning Glass Works, Corning, N.Y.) containing a 0.2 micron filter. Buffer used to rinse the membranes on the assay filters was prepared with purified water, but was not refiltered and was stored no longer than 5 days. Stock solutions of the drugs (usually 10 mM) were dissolved in 20 mM HEPES-KOH buffer pH 7.4 (assay buffer) with the addition of 1 to 5 μL of glacial AcOH, if needed, to keep them in solution. For eliprodil, the stock solution was buffer with the addition of 10% DMSO. All subsequent dilutions from stock were made in buffer.

Membrane Preparation

An extensively washed buffy coat membrane fraction was prepared from frozen adult rat forebrains (Zivic-Miller Laboratories, Inc, Zelienople, Pa.) as described previously (Coughenour L. L., Cordon J. J. *J. Pharmacol Exp. Ther.*, 1997;280:584–592) and stored at –80° C. On the day of the assay, pellets were resuspended in 35 mL of assay buffer at pH 7.4 using a Polytron setting 6. After incubation at 37° C. for 30 minutes in a shaking water bath, the homogenate was centrifuged 40,000×g for 10 minutes at 4° C. The pellets were resuspended in fresh buffer and centrifuged 3 more times before final suspension for use in the assay.

Binding Studies

[$^3$H]Ifenprodil Binding. Triplicate incubations were carried out in a volume of 0.5 mL in 1.3 mL polypropylene tubes (Marsh Biomedical Products Inc, Rochester, N.Y.) for 2 hours at room temperature. Incubations contained test agents, membranes (100–200 μg protein), and 4 nM [$^3$H]-ifenprodil in 20 mM HEPES-KOH buffer, pH 7.4 (assay buffer). Assays were started by addition of the membranes. Bound radioligand was separated by filtration under reduced pressure Using a Tomtec Mach II, 96-well cell harvester (Tomtec Inc, Orange, Colo.). Filtration was through Whatman GF/B glass fiber filters (Whatman Ltd, Maidstone, England), which had been soaked for at least 15 minutes in 0.3% polyethylenimine and allowed to air dry. The filters were rinsed with 3 mL of ice cold assay buffer within 6 seconds. Air was allowed to pass through the filters for an additional 10 seconds to remove residual moisture. The filter mat was supported on a cold (–20° C.) teflon support, and filters from individual wells were separated and placed in Mini Poly-Q vials (Beckman Instrrnents Inc, Fullerton, Calif.) and filled with 4 mL of scintillation cocktail (Beckman Ready Protein$^+$). Radioactivity retained on the filter was determined by liquid scintillation spectrophotometry. Nonspecific binding was defined as the binding in the presence of 1 mM ifenprodil. Specific binding was 90%.

[$^3$H]-TCP Binding. Binding assays were carried out essentially as described for [$^3$H]-ifenprodil binding. Incubations contained test agents, 100 to 200 μg protein, 2 nM [$^3$H]-TCP, and 10 μM glutamate, glycine, and spermnidine. Incubations were for 10 minutes to allow assays to be carried out under nonequilibrium conditions for the detection of binding selective to NMDA receptors of the NR2B subtype. Specific binding was defined as the binding displaced by 100 μM (+)MK-801 and was 90% of the total binding.

Data analysis. Binding curves were statistically analyzed for a best one or two site competition fit using GraphPad Prism software (GraphPad Software Inc, San Diego, Calif.). The normalized data was fit by nonweighted nonlinear regression to either $$y = \text{Bottom} + \frac{(\text{Top} - \text{Bottom})}{1 + 10^{x-\log EC_{50}}} \text{ or}$$

$$y = \text{Bottom} + (\text{Top} - \text{Bottom}) \frac{\text{Fraction-1}}{1 + 10^{x-\log EC_{50-1}}} + \frac{1 - \text{Fraction-1}}{1 + 10^{x-\log EC_{50-2}}}$$

Control data was entered as 100%, and no parameters were constrained. Inhibition curves were compared by ANOVA with post test comparisons of the $\log IC_{50}$ using Dunnett's multiple comparisons post test or Student's nonpaired, two-tailed t-test (GraphPad InStat software).

Materials. TCP, [piperidyl-3,4-$^3$H(N)]-(specific activity, 45 to 50 Ci/mmol) and ifenprodil, [phenyl-$^3$H]-(specific activity, 66.2 Ci/mmol) were purchased from Dupont NEN Research Products (Boston, Mass.). Ifenprodil tartrate, trifluperidol hydrochloride, and GBR-12909 dihydrochloride were purchased from Research Biochemicals International (Natick, Mass.). Spermidine trihydrochloride was purchased from United States Biochemical Corp (Cleveland, Ohio). HEPES, glutamate, and glycine were purchased from Sigma Chemical Co (St. Louis, Mo.). Haloperidol was obtained from McNeil Laboratories (Raritan, N.J.) or Research Biochemicals International. Eliprodil was synthesized by Thomas Malone (Parke-Davis Pharmaceutical Research, Ann Arbor, Mich.), and (+)MK-801 was synthesized by Leonard Lescosky (Parke-Davis Pharmaceutical Research, Ann Arbor, Mich.).

The electrophysiological assay results are set forth in Table 1.

6-OHDA Lesioned Rat Assay

6-Hydroxydopamine-lesioned rats were used (see Ungerstedt U., Arbuthnott G. W. Quantitative recording of rotational behavior in rats after 6-hydroxy-dopamine lesions of the nigrostraiatal dopamine system. *Brain Res.*, 1971;24(3): 485–93). Adult male Sprague-Dawley rats were anesthetized with chloral hydrate, and unilateral lesions of the nigrostriatal dopamine system were accomplished by infusion of 8 μg of 6-hydroxydopamine HBr (6-OHDA) into the right medial forebrain bundle. Rats were pretreated 30 minutes before surgery with desipramine HCl 25 mg/kg intraperitoneally (IP) to protect noradrenegic neurons, and pargyline 25 mg/kg IP to potentiate the effects of 6-OHDA. A minimum of 3 weeks after surgery, the rotational behavior induced by apomorphine HCl 50 μg/kg subcutaneously (SC) was assessed. Only rats demonstrating more than 100 contraversive turns/hour to apomorphine were used for the present experiments.

Rotational behavior was measured using an automatic rotometer system (Rotorat Rotational Activity System, MED Associates, Georgia, Vt.). Anti-parkinsonian activity was assessed as the ability of the compound to potentiate the contraversive rotation induced by L-DOPA methyl ester, 10 mg/kg SC, over a 6-hour period. Experiments were conducted using a crossover paradigm where each rat received either a vehicle plus L-DOPA, or the test compound plus L-DOPA, in randomized order. Rats were tested at 7-day intervals. In experiments in which the compound was tested orally, rats were food deprived for 16 hours. Statistical analysis between treatment groups were performed using a paired t-test. The results were reported in Table 1 as the minimum effective dose (MED) of compound (mg/kg) required to produce a statistically-significant increase in total contraversive rotations compared to rats receiving L-DOPA only.

TABLE 1

| Example | NR2A/NR2B Oocyte IC$_{50}$ ($\mu$M) | [$^3$H]Ifenprodil IC$_{50}$ ($\mu$M) |
|---|---|---|
| 1 | | 0.053 |
| 2 | 0.12 | |
| 3 | 1.0 | |
| 4 | | 0.091 |
| 5 | | 1.76 |
| 6 | | 0.73 |
| 7 | | >1 |
| 8a | 0.28 | |
| 8b | 0.12 | |

While the forms of the invention exemplified herein such as, for example, the name species of Formula I–III and the recitation of treatment of Parkinson's consitute presently preferred embodiments, many others are possible. It is not intended that said recited species of Formula I–III and preferred methods of use should, in any manner, limit or restrict the invention from the full scope claimed herein. It is not intended herein to name all of the possible equivalent forms or ramification of the invention. It is understood that the terms used herein are merely descriptive, rather than limiting. For example, the term "Parkinson's disease" is merely descriptive, and not limiting, of the term "neurodegenerative disease."

What is claimed is:

1. Heterocycle-substituted cyclohexylamines of Formula I and their pharmaceutically acceptable salts thereof:

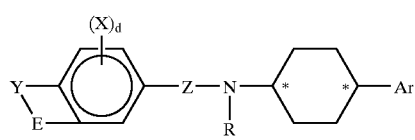

I wherein:
Ar is substituted 1 to 3 times or unsubstituted aryl or substituted 1 to 3 times or unsubstituted hereroaryl, which heteroaryl is from 5 to 14 atoms having from 1 to 2 heteroatoms selected from N, O, and S wherein the substituents are selected from the groups F, Cl, Br, I, OH, NH$_2$, SH, CN, NO$_2$, OCH$_3$, OC(O)CH$_3$, CF$_3$, OCH$_2$CH$_2$OH, NHC(O)CH$_3$, NHCH$_3$, or N(CH$_3$)$_2$;

—E—Y— is selected from the group consisting of
—CH═CH—N(H)—,
—(CH$_2$)$_2$—N(H)—,
—CH═N—N(H)—,
—C(O)—CH$_2$—N(H)—,
—CH$_2$—C(O)N(H)—,
—CH$_2$—S(O)—N(H)—,
—CH$_2$—S(O)$_2$—N(H)—,
—CH═CH—CH(OH)—,
—(CH$_2$—CH(OH)—,
—C(O)CH$_2$—C(O)—,
—C(O)—NH—C(O)—,
—N═CH—N(H)—,
—N(H)—C(O)—N(H)—,
—O—C(O)—NH—,
—S—C(O)NH—,
—O—N═CH(OH)—,
—S—N═CH(OH)—
—N═N—N(H)—,
—CH═CH—CH═C(OH)—
—(CH$_2$)$_3$—CH(OH)—,
—(CH$_2$)$_2$—S(O)N(H),
—(CH$_2$)$_2$—S(O)$_2$—N(H)—,
—CH═CH—C(O)—N(H)—,
—C(O)—NH—N═C(OH)—,
—CH═N—NH—C(O),
—CH═N(O)—N═C(OH)—,
—N(H)—C(O)—N(H)C(O)—,
—N═CH—C(O)NH—,
—O—CH$_2$—C(O)—NH—,
—S—CH$_2$—C(O)—NH—, and
—N(H)—C(O)C(O)—N(H)—;

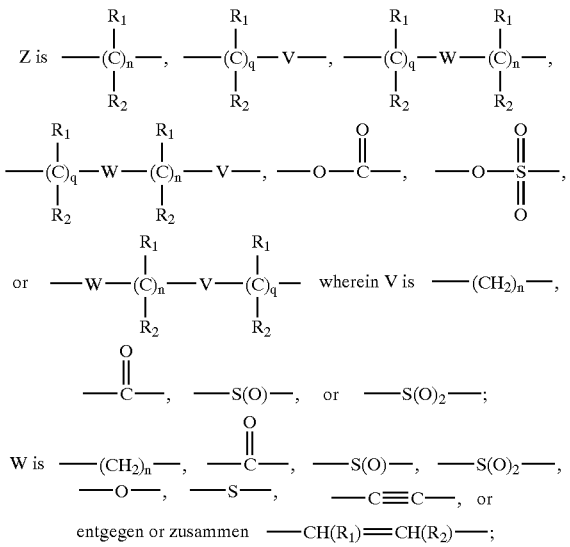

d is an integer from 0 to 2;
n is an integer from 1 to 6;
q is an integer from 0 to 6;
R$_1$ and R$_2$ are independently selected from the group consisting of hydrogen, alkyl, OH, hydroxyalkyl, aminoalkyl, aralkyl, or N(R$_4$)(R$_5$) wherein R$_4$ and R$_5$ are independently selected from hydrogen, alkyl, aralkyl, heteroaryl, heteroaralkyl, aminoalkyl, hydroxyalkyl, and thioalkyl;
R is hydrogen, alkyl, C(O)R$_6$, C(O)OR$_6$, C(O)NHR$_6$, -alkyl—C(O)NH$_2$, aralkyl, (C$_3$–C$_7$ cyclo-alkyl)-alkyl, hydroxyalkyl, aminoalkyl, amino(hydroxy)alkyl, carboxyalkyl, heteroaraayl, alkenylalkyl, or OH wherein R$_6$ is alkyl or aralkyl;
X is independently selected from hydrogen or an electron withdrawing group; and
* denotes cis or trans or a mixture thereof.

2. A compound according to claim 1 wherein:
X is independently selected from hydrogen or an electron withdrawing group selected from the group consisting of halogen, nitro, cyano, aminoalkyl CF$_3$, C(O)CH$_3$, and haloalkyl.

3. The compound according to claim 1 wherein:

Ar is unsubstituted or substituted phenyl;

—E—Y— is selected from —O—C(=O)—NH—,

—S—C(=O)—NH—, —CH=CH—NH—,

—N=CH—NH—, —NH—C(=O)—NH,

—N=N—NH—, and —NH—C(=O)—C(=O)—NH—;

X is independently selected from hydrogen or an electron withdrawing group selected from the group consisting of halogen, nitro, cyano, aminoalkyl $CF_3$, $C(O)CH_3$, and haloalkyl; and

* denotes trans.

4. The compound according to claim 1 wherein:

Ar is unsubstituted or substituted phenyl;

—E—Y— is selected from —O—C(=O)—NH—,

—S—C(=O)—NH—, —CH=CH—NH—,

—N=CH—NH—, —NH—C(=O)—NH,

—N=N—NH—, and —NH—C(=O)—C(=O)—NH—;

Z is a group whereby Ar and the nitrogen atom in Formula I are separated by from 2 to 4 atoms;

X is independently selected from hydrogen or an electron withdrawing group selected from the group consisting of halogen, nitro, cyano, aminoalkyl, $CF_3$, $C(O)CH_3$, and haloalkyl; and

* denotes trans.

5. The compound according to claim 1 wherein:

Ar is unsubstituted or substituted phenyl;

—E—Y— is selected from —O—C(=O)—NH—,

—S—C(=O)—NH—, —CH=CH—NH—,

—N=CH—NH—, —NH—C(=O)—NH,

—N=N—NH—, and —NH—C(=O)—C(=O)—NH—;

Z is —$CH_2$—$(CH_2)_m$—, —$(CH_2)_m$—C(=O)—,

—O—$(CH_2)_m$—, —$(CH_2)_m$—CH(CH_3)—,

—$(CH_2)_m$—CH(OH)—$CH_2$—, —O—C(C_3H, CH_3)(=O)—,

—S—$(CH_2)_m$—, —C≡C—$CH_2$—, or

—C≡C—$(CH_2)_2$— wherein m is an integer from 1 to 3;

R is hydrogen, methyl, $C(O)CH_3$, heteroaralkyl, ($C_3$–$C_7$ cycloalkyl) alkyl, $H_2NC(O)$ alkyl, or alkenylalkyl;

X is hydrogen; and

* denotes trans.

6. A compound according claim 1 and selected from:

6-[3-(trans-4-Phenylcyclohexylamino)propyl]-3H-benzoxazol-2-one;

6-{3-[trans-4-(4-Fluorophenyl)cyclohexylamino] propyl}-3H-benzoxazol-2-one;

6-[2-(trans-4-Phenylcyclohexylamino)ethylsulfanyl]-3H-benzoxazol-2-one;

5-{1-Hydroxy-2-[methyl(trans-4-phenylcyclohexyl) amino]ethyl}-1,3-dihydrobenzimidazol-2-one;

6-(3-{[trans-4-(4-Fluorophenyl)cyclohexyl] methylamino}propyl)-3H-benzoxazol-2-one;

6-(3-{[trans-4-(4-Fluorophenyl)cyclohexyl] ethylamino}propyl)-3H-benzoxazol-2-one;

5-[2-(cis-4-Phenylcyclohexylamino)ethoxy]-1, 3dihydrobenzimidazol-2-one;

5-[2-(trans-4-Phenylcyclohexylamino)ethoxy]-1,3-dihydrobenzmidazol-2-one; and

6-{Methyl[2-(trans-4-phenylcyclohexylanmino)ethyl] amino}-3H-benzoxazol-2-one.

7. A compound of Formula II

II or a pharmaceutically acceptable salt thereof
wherein:

Ar is substituted 1 to 3 times or unsubstituted aryl or substituted 1 to 3 times or unsubstituted hereroaryl, which heteroaryl is from 5 to 14 atoms having from 1 to 2 heteroatoms selected from N, O, and S wherein the substituents are selected from the groups F, Cl, Br, I, OH, $NH_2$, SH, CN, $NO_2$, $OCH_3$, $OC(O)CH_3$, $CF_3$, $OCH_2CH_2OH$, $NHC(O)CH_3$, $NHCH_3$, or $N(CH_3)_2$;

—E—Y— is selected from the group consisting of
—CH=CH—N(H)—,
—$(CH_2)_2$—N(H)—,
—CH=N—N(H)—,
—C(O)—$CH_2$—N(H)—,
—$CH_2$—C(O)N(H)—,
—$CH_2$—S(O)—N(H)—,
—$CH_2$—$S(O)_2$—N(H)—,
—CH=CH—CH(OH)—,
—$(CH_2)_2$—CH(OH)—,
—C(O)—$CH_2$—C(O)—,
—C(O)—NH—C(O)—,
—N=CH—N(H)—,
—N(H)—C(O)—N(H)—,
—O—C(O)—NH—,
—S—C(O)—NH—,
—O—N=CH(OH)—, —S—N=CH(OH)—,
—N=N—N(H)—,
—CH=CH—CH=C(OH)—,
—(CH$_2$)$_3$—CH(OH)—,
—(CH$_2$)$_2$—S(O)—N(H)—,
—(CH$_2$)$_2$—S(O)$_2$—N(H)—,
—CH=CH—C(O)—N(H)—,
—C(O)—NH—N=C(OH)—,
—CH=N—NH—C(O),
—CH=N(O)—N=C(OH)—,
—N(H)—C(O)—N(H)—C(O)—,
—N=CH—C(O)—NH—,
—O—CH$_2$—C(O)—NH—,
—S—CH$_2$—C(O)—NH—, and
—N(H)—C(O)—C(O)—N(H)—;

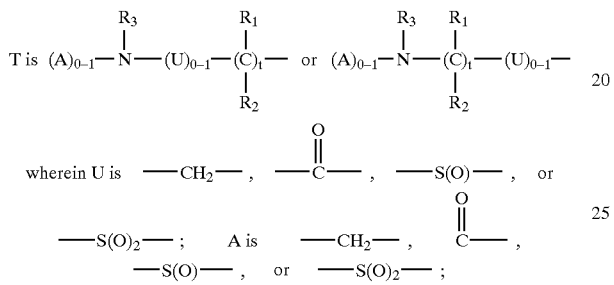

wherein U is —CH$_2$—, —C(O)—, —S(O)—, or —S(O)$_2$—; A is —CH$_2$—, —C(O)—, —S(O)—, or —S(O)$_2$—;

d is an integer from 0 to 2;

t is an integer from 1 to 3;

R$_1$ and R$_2$ are independently selected from hydrogen, alkyl, OH, hydroxyalkyl, aminoalkyl, thioalkyl, aryl, aralkyl, heteroaryl, heteroaralkyl, guanidinyl, (aminocarbonyl)alkyl-, carboxyalkyl-, (methylthio)-alkyl-, or N(R$_4$)(R$_5$) wherein R$_4$ and R$_5$ are independently selected from hydrogen, alkyl, aralkyl, heteroaryl, heteroaralkyl, ureidoalkyl, aminoalkyl, hydroxyalkyl, or thioalkyl;

R$_3$ is hydrogen, alkyl, OH, or aralkyl;

R is hydrogen, alkyl, C(O)R$_6$, C(O)OR$_6$, C(O)NHR$_6$, -alkyl-C(O)NH$_2$, aralkyl, (C$_3$–C$_7$ cyclo-alkyl)-allyl, hydroxyalkyl, aminoalkyl, amino(hydroxy)alkyl, carboxyalkyl, heteroaralkyl, alkenylalkyl, or OH wherein R$_6$ is alkyl or aralkyl;

X is independently selected from hydrogen or an electron withdrawing group; and

* denotes cis or trans or a mixture thereof.

8. The compound according to claim 7 wherein:

X is independently selected from hydrogen or an electron withdrawing group selected from the group consisting of halogen, nitro, cyano, aminoalkyl, CF$_3$, C(O)CH$_3$, and haloalkyl.

9. The compound according to claim 7 wherein:

Ar is unsubstituted or substituted phenyl;

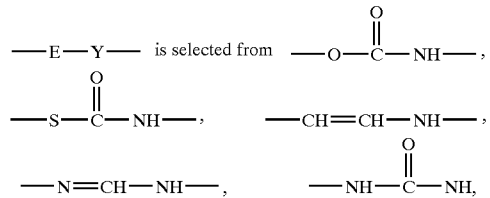

X is independently selected from hydrogen or an electron withdrawing group selected from the group consisting of halogen, nitro, cyano, aminoalkyl, CF$_3$, C(O)CH$_3$, and haloalkyl; and

* denotes trans.

10. The compound according to claim 7 wherein:

Ar is unsubstituted or substituted phenyl;

Ar and the nitrogen atom bearing R are separated by 3 or 4 atoms;

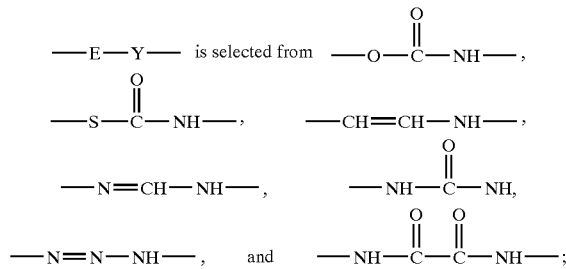

X is independently selected from hydrogen or an electron withdrawing group selected from the group consisting of halogen, nitro, cyano, aminoalkyl, CF$_3$, C(O)CH$_3$, and haloalkyl; and

* denotes trans.

11. The compound according to claim 7 wherein:

Ar is unsubstituted or substituted phenyl;

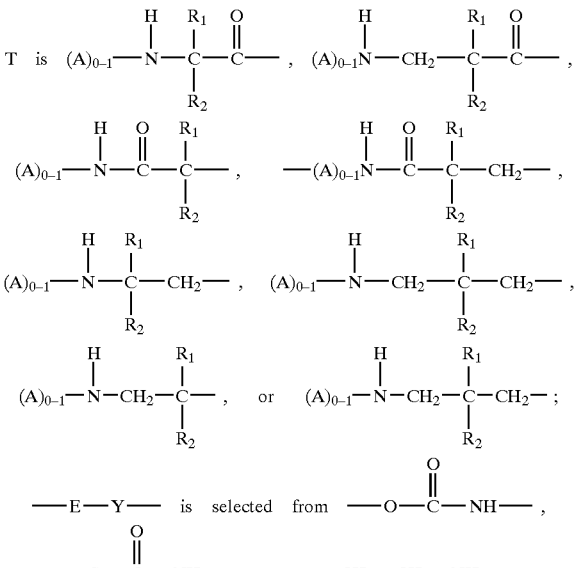

R is hydrogen, methyl, —C(O)CH$_3$, H$_2$NC(O) alkyl, alkenylalkyl, (C$_3$–C$_7$ cycloalkyl) alkyl or heteroaralkyl;

X is hydrogen; and

* denotes trans.

12. The compound according to claim 7 named 6-{methyl-[2-(4-phenyl-cyclohexylamino)ethyl]-amino}-3H-benzoxazol-2-one.

13. A compound of Formula III

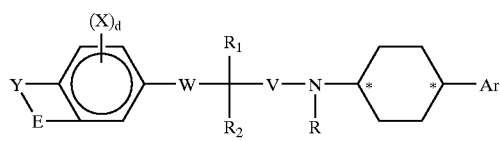

wherein:

- Ar is substituted 1 to 3 times or unsubstituted aryl or substituted 1 to 3 times or unsubstituted heteroaryl, which heteroaryl is from 5 to 14 atoms having from 1 to 2 heteroatoms selected from N, O, and S wherein the substituents are selected from the groups F, Cl, Br, I, OH, $NH_2$, SH, CN, $NO_2$, $OCH_3$, $OC(O)CH_3$, $CF_3$, $OCH_2CH_2OH$, $NHC(O)CH_3$, $NHCH_3$, or $N(CH_3)_2$;
- —E—Y— is selected from the group consisting of
  —CH═CH—N(H)—,
  —(CH₂)₂—N(H)—,
  —CH═N—N(H)—,
  —C(O)CH₂—N(H)—,
  —CH₂—C(O)—N(H)—,
  —CH₂—S(O)—N(H)—,
  —CH₂—S(O)₂—(H)—,
  —CH═CH—CH(OH)—,
  —(CH₂)₂—CH(OH)—,
  —C(O)—CH₂—C(O)—,
  —C(O)NH—C(O)—,
  —N═CH—N(H)—,
  —N(H)—C(O)N(H)—,
  —O—C(O)—NH—,
  —S—C(O)—NH—,
  —O—N═CH(OH)—,
  —S—N═CH(OH)—,
  —N═N—N(O)—,
  —CH═CH—CH═C(OH—,
  —(CH₂)₃—CH(OH)—,
  —(CH₂)₂—S(O)—N(H)—,
  —(CH₂)₂—S(O)₂—N(H)—,
  —CH═CH—C(O)—N(H)—,
  —C(O)—NH—N═C(OH)—,
  —CH═N—NH—C(O),
  —CH═N(O)—N═C(OH)—,
  —N(H)—C(O)—N(H)—C(O)—,
  —N═CH—C(O)—N(H)—,
  —O—CH₂—C(O)—NH—,
  —S—CH₂—C(O)—NH—, and
  —N(H)—C(O)—C(O)—N(H)—;

wherein V is —(CH₂)ₙ—, —C(O)—, —S(O)—, or —S(O)₂—; W is —(CH₂)ₙ—, —C(O)—, —S(O)—, —S(O)₂—, —O—, —S—, —C≡C—, or entgegen or zusammen —CH(R₁)═CH(R₂)—;

d is an integer from 0 to 2;

n is an integer from 1 to 6;

q is an integer from 0 to 6;

$R_1$ and $R_2$ are independently selected from the group consisting of hydrogen, alkyl, OH, hydroxyalkyl, aminoalkyl, aralkyl, or $N(R_4)(R_5)$ wherein $R_4$ and $R_5$ are independently selected from hydrogen, alkyl, aralkyl, heteroaryl, heteroaralkyl, aminoalkyl, hydroxyalkyl and thioalkyl;

R is hydrogen, alkyl, $C(O)R_6$, $C(O)OR_6$, $C(O)NHR_6$, -alkyl—$C(O)NH_2$, aralkyl, ($C_3$–$C_7$ cyclo-alkyl)-alkyl, hydroxyalkyl, aminoalkyl, amino(hydroxy)alkyl, carboxyalkyl, heteroaralkyl, alkenylalkyl, or OH wherein $R_6$ is alkyl or aralkyl;

X is independently selected from hydrogen or an electron withdrawing group; and

* denotes cis or trans or a mixture thereof.

14. A compound according to claim 13 wherein:

X is independently selected from hydrogen or an electron withdrawing group selected from the group consisting of halogen, nitro, cyano, aminoalkyl, $CF_3$, $C(O)CH_3$, and haloalkyl.

15. The compound according to claim 13 wherein:

Ar is unsubstituted or substituted phenyl;

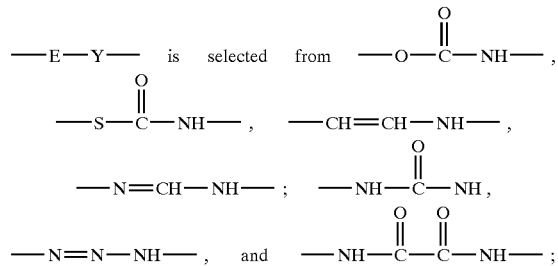

X is independently selected from hydrogen or an electron withdrawing group selected from the group consisting of halogen, nitro, cyano, aminoalkyl, $CF_3$, $C(O)CH_3$, and haloalkyl; and

* denotes cis.

16. The compound according to claim 13 wherein:

Ar is unsubstituted or substituted phenyl;

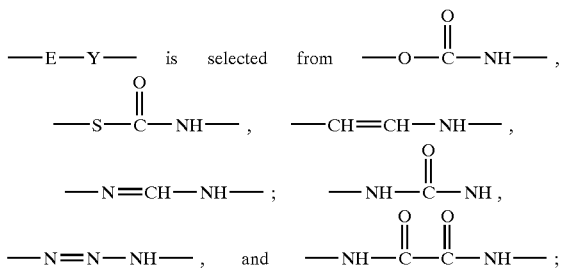

X is independently selected from hydrogen or an electron withdrawing group selected from the group consisting of halogen, nitro, cyano, aminoalkyl, $CF_3$, $C(O)CH_3$, and haloalkyl; and

* denotes trans.

17. The compound of claim 1 wherein * denotes cis.

18. The compound of claim 7 wherein * denotes cis.

19. The compound of claim 13 wherein * denotes cis.

20. A pharmaceutical composition useful for treating disorders responsive to the selective blockade of N-methyl-D-aspartate receptor subtypes, optionally disorders as stroke, cerebral ischemia, trauma, hypoglycemia, neurodegenerative disorders, anxiety, depression, migraine headache, convulsions, aminoglycoside antibiotics-induced hearing loss, psychosis, glaucoma, CMV retinitis, opioid tolerance or withdrawal, chronic pain, or urinary incontinence the compositions comprising a pharmaceutically acceptable carrier or diluent and a therapeutically effective amount of at least one compound of claim 1 or claim 7 or claim 13.

21. The pharmaceutical composition according to claim 20, wherein the neurodegenerative disorder is Parkinson's disease.

22. The pharmaceutical composition according to claim 20, further comprising a dopamine agonist or precursor thereof in amount effective to treat Parkinson's disease.

23. A method for treating disorders responsive to the selective blockade of N-methyl-D-aspartate receptor subtypes in a mammal suffering thereof which comprises administering in unit dosage form at least one compound represented by Formula I of claim 1 or Formula II of claim 7 or Formula m of claim 13.

24. The method according to claim 23, wherein the disorder is Parkinson's disease.

25. The method according to claim 23, further comprising administering in unit dosage form a compound any one of Formula I–III to a mammal suffering from Parkinson's disease.

* * * * *

UNITED STATES PATENT AND TRADEMARK OFFICE
CERTIFICATE OF CORRECTION

PATENT NO. : 6,683,101 B2
DATED : January 27, 2004
INVENTOR(S) : Russell Joseph Deorazio et al.

It is certified that error appears in the above-identified patent and that said Letters Patent is hereby corrected as shown below:

Column 32,
Line 58, "carboxyalkyl, heteroaraayl, alkenylalkyl, or OH" should read
-- carboxyalkyl, heteroaralkyl, alkenylalkyl, or OH --

Column 35,
Line 43, "-alkyl-C(O)NH$_2$, aralkyl, (C$_3$-C$_7$ cyclo-alkyl)-allyl," should read
-- -alkyl-C(O)NH$_2$, aralkyl, (C$_3$-C$_7$ cyclo-alkyl)-alkyl, --

Column 37,
Line 32, "-CH$_2$-S(O)$_2$-(H)-" should read -- -CH$_2$-S(O)$_2$-N(H)- --
Line 43, "-N=N-N(O)-" should read -- -N=N-N(H)- --

Column 40,
Line 10, "7 or Formula m of claim 13" should be -- 7 or Formula III of claim 13 --

Signed and Sealed this

Twenty-first Day of September, 2004

JON W. DUDAS
*Director of the United States Patent and Trademark Office*